US009365623B2

(12) United States Patent
Ulijasz et al.

(10) Patent No.: US 9,365,623 B2
(45) Date of Patent: Jun. 14, 2016

(54) CYANOCHROME FLUOROPHORES

(71) Applicant: WISCONSIN ALUMNI RESEARCH FOUNDATION, Madison, WI (US)

(72) Inventors: Andrew T. Ulijasz, Twickenham (GB); Richard D. Vierstra, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 14/464,751

(22) Filed: Aug. 21, 2014

(65) Prior Publication Data

US 2015/0056646 A1   Feb. 26, 2015

Related U.S. Application Data

(62) Division of application No. 12/789,112, filed on May 27, 2010, now Pat. No. 8,822,162.

(60) Provisional application No. 61/181,578, filed on May 27, 2009.

(51) Int. Cl.

| | | |
|---|---|---|
| *C12Q 1/00* | (2006.01) |
| *C12Q 1/02* | (2006.01) |
| *C07H 21/00* | (2006.01) |
| *C12N 15/00* | (2006.01) |
| *C12N 15/31* | (2006.01) |
| *C12N 1/20* | (2006.01) |
| *C12N 1/14* | (2006.01) |
| *C12N 1/16* | (2006.01) |
| *C12N 5/10* | (2006.01) |
| *C07K 14/195* | (2006.01) |
| *A61K 49/00* | (2006.01) |
| *G01N 33/50* | (2006.01) |
| *G01N 33/542* | (2006.01) |

(52) U.S. Cl.
CPC ........... *C07K 14/195* (2013.01); *A61K 49/0045* (2013.01); *C12Q 1/02* (2013.01); *G01N 33/5035* (2013.01); *G01N 33/542* (2013.01)

(58) Field of Classification Search
None
See application file for complete search history.

(56) References Cited

U.S. PATENT DOCUMENTS

| | | |
|---|---|---|
| 5,491,084 A | 2/1996 | Chalfie et al. |
| 6,046,014 A | 4/2000 | Lagarias et al. |
| 8,822,162 B2 | 9/2014 | Ulijasz et al. |
| 2003/0134787 A1 | 7/2003 | Rothman et al. |
| 2009/0061444 A1 | 3/2009 | Ulijasz et al. |

FOREIGN PATENT DOCUMENTS

WO   2010/138727   12/2010

OTHER PUBLICATIONS

Sang, H., Mechanisms of Development 121:1179-1186, 2004.*
User Manual for pBAD/Myc-His A, B, and C, Dec. 2010.*
Allewalt et al., "Effect of temperature and light on growth of and photosynthesis by synechococcus isolates typical of those predominating in the octopus spring microbial mat community of Yellowstone National Park," Appl. Environ. Microbiol. (2006) 72(1):544-550.
Altschul et al, "Gapped BLAST and PSI-BLAST: a new generation of protein database search programs," Nucl. Acids .Res. (1997) 25(17):3389-3402.
Ausubel et al., Current Protocols in Molecular Biology, John Wiley & Sons, Inc., (1993) vols. 1-5, Table of Contents, 14 pages.
Becke, "Density-functional thermochemistry. III. The role of exact exchange," J. Chem. Phys. (1993) 989(7):5648-5652.
Bhaya et al., "Population level functional diversity in a microbial community revealed by comparative genomic and metagenomic analyses," ISME J. (2007) 1:703-713.
Bhoo et al., "Phytochrome photochromism probed by site-directed mutations and chromophore esterification," J. Amer. Chem. Soc. (1997) 119:11717-11718.
Bhoo et al., "Bacteriophytochromes are photochromic histidine kinases using a biliverdin chromophore," Nature (2001) 414:776-779.
Borucki et al., "Light-induced proton release of phytochrome is coupled to the transient deprotonation of the tetrapyrrole chromophore," J. Biol. Chem. (2005) 280(40):34358-34364.
Collins et al., "A preliminary solubility screen used to improve crystallization trials: crystallization and preliminary x-ray structure determination of aeropyrum pernix flap endonuclease-1," Acta. Crystallogr. D. Biol. Crystallogr. (2004) 60:1674-1678.
Davis, S.J. et al., "Bacteriophytochromes: phytochrome-like photoreceptors from nonphotosynthetic eubacteria," Science (1999) 286(5449):2517-2520.
Delaglio et al., "NMRPipe: a multidimensional spectral processing system based on UNIX pipes," J. Biomol. NMR (1995) 6:277-293.
Esteban et al., "Ligh-induced conformational changes of cyanobacterial phtochrome Cph1 probed by limited proteolysis and autophosphorylation," Biochem. (2005) 44:450-461.
Fischer et al., "Harnessing phytochrome's glowing potential," Proc. Natl. Acad. Sci. USA (2004) 101(50):17334-17339.
Fischer et al., "Multiple roles of a conserved GAF domain tyrosine residue in cyanobacterial and plant phytochromes," Biochem. (2005) 44:15203-15215.
Gambetta et al., "Genetic engineering of phytochrome biosynthesis in bacteria," Proc. Natl. Acad. Sci. USA (2001) 98(19):10566-10571.
GenBank Accession No. BAC08476, GI:22294647, "t1r0924 [Thermosynechococcus elongatus BP-1], Dec. 2007, 2 pages.
Hahn et al., "Probing protein-chromophore interactions in Cph1 phytochrome by mutagenesis," FEBS J. (2006) 273:1415-1429.

(Continued)

*Primary Examiner* — David J Steadman
(74) *Attorney, Agent, or Firm* — Michael Best & Friedrich LLP

(57) ABSTRACT

Genetically-engineered cyanochrome fluorophore molecules (fluorophores) with increased fluorescence and with absorbing fluorescence in the blue and green (blue/green) portion of the light spectrum are provided. These fluorophores are derived from the domains of phytochromes, and in particular cyanobacterial phytochromes. Methods for generating these fluorophores and various applications of these fluorophores are also provided.

16 Claims, 9 Drawing Sheets

(56) References Cited

OTHER PUBLICATIONS

Ikeuchi, M. et al., "Cyanobacterioshromes: a new superfamily of tetrapyrrole-binding photoreceptors in cyanobacteria," Photochem. Photobiol. Sci. (2008) 7:1159-1167.

Ishizuka, T. et al., "Characterization of cyanobacteriochrome TePixJ from a thermophilic cyanobacterium thermosynechococcus elongatus strain BP-1," Plant Cell Physiol. (2006) 47(9):1251-1261.

Karlin et al., "Methods for assessing the statistical significance of molecular sequence features by using general scoring schemes," Proc. Natl. Acad. Sci. USA (1990) 87:2264-2268.

Karniol et al., "Phylogenetic analysis of the phytochrome superfamily reveals distinct microbial subfamilies of photoreceptors," Biochem. J. (2005) 392:103-116.

Karniol et al., "The pair of bacteriophytochromes from agrobacterium tumefaciens are histidine kinases with opoposing photobiological properties," Proc. Natl. Acad. Sci. USA (2003) 100(5):2807-2812.

Karniol et al., "Structure, function, and evolution of microbial phytochromes," Photomorphogenesis in Plants and Bacteria, 3rd Edition (2006) 65-98.

Keppler et al., "Labeling of fusion proteins with synthetic fluorophores in live cells," Proc. Natl. Acad. Sci. USA (2004) 101(27):9955-9959.

Kneip et al., "Protonation state and structural changes of the tetrapyrrole chromophore during the Pr→Pfr photogransformation of phytochrome: a resonance raman spectroscopic study," Biochem. (1999) 38:15185-15192.

Kriegler, Gene Transfer and Expression: a Laboratory Manual, M. Stockton Press (1990) Table of contents, 6 pages.

Lin, J. et al., "Whole-genome shotgun optical mapping of deinococcus radiodurans," Science (1999) 285(5433):1558-1562.

Magdo et al., "Calculation of vibrational spectra of linear tetrapyrroles. I. Global sets of scaling factors for force fields derived by ab initio and density functional theory methods," J. Phys. Chem. A (1999) 103:289-303.

Malhotra et al., "Identification of chromophore binding domains of yeast DNA photolyase," J. Biol. Chem. (1992) 267(5):2909-2914.

Meier, "Vibrational spectroscopy: a vanishing discipline," Chem. Soc. Rev. (2005) 34:734-752.

Miller et al., "Single-molecule dynamics of phytochrome-bound fluorophores probed by fluorescence correlation spectroscopy," Proc. Natl. Acad. Sci. USA (2006) 103(30):11136-11141.

Mroginski et al., "Calculation of the vibrational spectra of linear tetrapyrroles 2. Resonance raman spectra of hexamethylpyrromethene monomers," J. Phys. Chem. B (2000) 104:10885-10899.

Mroginski et al., "Determination fo the chromophore structures in the photoinduced reaction cycle of phytochrome," J. Am. Chem. Sco. (2004) 126:16734-16735.

Mroginski et al., "The chromophore structural changes during the photocycle of phytochrome: a combined resonance raman and quantum chemical approach," Acc. Chem. Res. (2007) 40(4):258-266.

Murphy et al., "The phytofluors: a new class of fluorescent protein probes," Curr. Biol. (1997) 7:870-876.

Nakamura, Y. et al., SwissProt Accession No. Q8DLC7, Oct. 31, 2006, retrieved from the internet Aug. 20, 2010, http://www.ncbi.nlm.nih.gov/protein/81743662.

Oka et al., "Functional analysis of a 450-amino acid N-terminal fragment of phytochrome B in arabidopsis," Plant Cell (2004) 16:2104-2116.

Park et al., "A second photochromic bacteriophytochrome from Synechocystis sp. PCC 6803: spectral analysis and down-regulation by light," Biochem. (2000) 39:10840-10847.

Pearson et al., "Improved tools for biological sequence comparison," Proc. Natl. Acad. Sci. USA (1988) 85:2444-2448.

Quail, "An emerging molecular map of the phytochromes," Plant Cell Environ. (1997) 20:657-665.

Remberg et al., "Raman spectroscopic and light-induced kinetic characterization of a recombinant phytochrome of the cyanobacterium synechocystis," Biochem. (1997) 36:13389-13395.

Remberg et al., "Differential effects of mutations in the chromophore pocket of recombinant phytochrome of chromoprotein assembly and Pr-to-Pfr photoconversion," Eur. J. Biochem. (1999) 266:201-208.

Rockwell, N.C. et al., "A second conserved GAF domain cysteine is required for the blue/green photoreversibility of cyanobacteriochrome T1r0924 from thermosynechococcus elongatus," Biochem. (2008) 47:7304-7316.

Rohmer et al., "15N Mas NMR studies of Cph1 phytochrome: chromophore dynamics and intramolecular signal transduction," J. Phys. Chem. B. (2006) 110:20580-20585.

Sambrook et al., Molecular Cloning, a Laboratory Manual, 2nd Edition, Cold Spring Harbor Laboratory Press (1989) Table of contents, 30 pages.

Sawers et al., "Diversity of phytochrome chromophores," Plant Phys. Online, http://4eplantphys.net/article.php, (2006) pp. 1-5.

Scheer, "Model compounds for the phytochrome chromophore," Techniques in Photomorphogenesis (1984) 227-256.

Schmitz, O. et al., "CikA, a bacteriophytochrome that resets the cyanobacterial circadian clock," Science (2000) 289:765-768.

Shaner et al., "Improved monomeric red, orange and yellow fluorescent proteins derived from Discosoma sp. red fluorescent protein," Nature Biotech. (2004) 22(12):1567-1572.

Sharrock, R.A. et al., "novel phytochrome sequences in arabidopsis thaliana: structure, evolution, and differential expression of a plant regulatory photoreceptor family," Genes & Dev. (1989) 3:1745-1757.

Shu et al., "Mammalian expression of infrared fluorescent proteins engineered from a bacterial phytochrome," Science (2009) 324:804-807.

Steunou et al., "In situ analysis of nitrogen fixation and metabolic switching in unicellular thermophilic cyanobacteria inhabiting hot spring microbial mats," Proc. Natl. Acad. Sci. USA (2006) 103(7):2398-2403.

Strauss et al., "Heteronuclear solution-state NMR studies of the chromophore in cyanobacterial phytochrome Cph1," Biochem. (2005) 44:8244-8250.

Ulijasz et al., "A vancomycin-inducible LacZ reporter system in bacillus subtilis: induction by antibiotics that inhibit cell wall synthesis and by lysozyme," J. Bacteriol. (1996) 178(21):6305-6309.

Ulijasz, A.T. et al., "Characterization of two thermostable cyanobacterial phytochromes reveals global movements in the chromophore-binding domain during photoconversion," J. Biol Chem. (2008) 283(30):21251-21266.

Ulijasz, A.T. et al., "The cyanochromes: blue-green photoreversible photoreceptors defined by a stable double cysteine linkage to a phycoviolobilin-type chromophore," J. Biol. Chem. (2009( 284:29757-29772, retrieved from the Internet: https://mywebspace.wisc.edu/gcornilescu/web/pixj_jbc.pdf.

UnitProtKB Accession No. P74111, Apr. 2008, 2 pages.

UnitProtKB Accession No. P14712, May 2008, 4 pages.

Venters et al., "Uniform 13C isotope labeling of protein with sodium acetate for NMR studies: application to human carbonic anhydrase II," Biochem. (1991) 30:4491-4494.

Vierstra et al., "Phytochromes in microorganisms," Handbook of Photosensory Receptors (2005) 171-196.

Von Stetten et al., "Highly conserved residues Asp-197, and His-250 in Agp1 photochrome control the proton affinity of the chromophore and Pfr formation," J. Biol. Chem. (2007) 282(3):2116-2123.

Wagner et al., "A light-sensing knot revealed by the structure of the chromophore-binding domain of phytochrome," Nature (2005) 438:325-331.

Wagner et al., "High resolution structure of deinococcus bacteriophytochrome yields new insights into phytochrome architecture and evolution," J. Biol. Chem. (2007) 282(16):12298-12309.

Wagner et al., "Mutational analysis of deinococcus radiodurans bacteriophytochrome reveals key amino acids necessary for the photochromicity and proton exchange cycle of phytochromes," J. Biol. Chem. (2008) 283(18):12212-12226.

Wang et al., "Conditional stability of the HemA protein (glutamyl-tRNA reductase) regulates heme biosynthesis in Salmonella typhimurium," J. Bacteriol. (1999) 181(4):1211-1219.

Wang et al., "Evolution of new nonantibody proteins via iterative somatic hypermutation," Proc. Natl. Acad. Sci. USA (2004) 101(48):16745-16749.

(56) References Cited

OTHER PUBLICATIONS

Wellems, T.E. et al., "Homologous genes encode two distinct histidine-rich proteins in a cloned isolate of plasmodium falciparum," Proc. Natl. Acad. Sci. USA (1986) 83:6065-6069.

Wikipedia, "Conserved sequence" http://en.wikipedia.org/wiki/Conserved_sequence, downloaded Jan. 24, 2012 (3 pages).

Wu et al., "Defining the bilin lyase domain: lessons from the extended phytochrome superfamily," Biochem. (2000) 39:13487-13495.

Wurm, "Production of recombinant protein therapeutics in cultivated mammalian cells," Nat. Biotech. (2004) 22:1393-1398.

International Search Report and Written Opinion for Application No. PCT/US2010/36421 dated Oct. 20, 2010 (9 pages).

Von Stetten et al., Highly conserved residues 0197 and H250 in Agp1 phytochrome control the proton affinity of the chromophore and Pfr formation, 2007, J. Biol. Chem., vol. 282, pp. 2116-2123, published online Nov. 22, 2006.

Zheng et al., "An efficient one-step site-directed and site-saturation mutagenesis protocol," Nucleic Acids Res., 32:e115, 5 pages, 2004.

Rockwell et al., "Phytochome Structure and Signaling Mechanisms," 2006, Annu. Rev. Plant Biol. 57:837-858.

Yoshihara et al., "Cyanobacterial phytochrome-like PixJ1 holoprotein shows novel reversible photoconversion between blue- and green-absorbing forms," 2004, Plant Cell Physiol. 45:1729-1737.

Ishizuka et al., "Cyanobacteriochrome TePixJ of Thermosynechococcus elongatus harbors phycoviolobilin as a chromophore," 2007, Plant Cell Physiol. 48:1385-1390.

Thompson et al., "Clustal W: improving the sensitivity of progressive multiple sequence alignment through sequence weighting, position-specific gap penalties and weight matrix choice," 1994, Nucleic Acids Res. 22:4673-4680.

Pollastri et al., "Improving the prediction of protein secondary structure in three and eight classes using recurrent neural networks and profiles," 2002, Proteins 47:228-235.

Rodriguez et al., "A copper cofactor for the ethylene receptor ETR1 from Arabidopsis," 1999, Science 283:996-998.

Bhaya et al., "Light regulation of type IV pilus-dependent motility by chemosensor-like elements in Synechocystis PCC6803," 2001, Proc. Natl. Acad. Sci. USA 98:7540-7545.

Terauchi et al., "RcaE is a complementary chromatic adaptation photoreceptor required for green and red light responsiveness," 2004, Mol. Microbiol., 567-77.

Yeh et al., "A Cyanobacterial Phytochrome Two-Component Light Sensory System," 1997, Science, vol. 277, No. 5331, pp. 1505-1508.

Thor et al., "Chromophore structure in the photocycle of the cyanobacterial phytochrome Cph1," 2006, Biophys. J. 91:1811-1822.

United States Patent Office Action for U.S. Appl. No. 12/789,112 dated Jun. 2, 2011 (30 pages).

United States Patent Office Action for U.S. Appl. No. 12/789,112 dated Nov. 1, 2011 (13 pages).

United States Patent Office Action for U.S. Appl. No. 12/167,222 dated May 25, 2010 (10 pages).

United States Patent Office Action for U.S. Appl. No. 12/167,222 dated Nov. 12, 2010 (11 pages).

United States Patent Office Action for U.S. Appl. No. 12/167,222 dated May 11, 2011 (6 pages).

United States Patent Office Action for U.S. Appl. No. 12/167,222 dated Sep. 26, 2011 (19 pages).

United States Patent Office Action for U.S. Appl. No. 12/167,222 dated May 24, 2012 (23 pages).

United States Patent Office Notice of Allowance for U.S. Appl. No. 12/789,112 dated Apr. 30, 2014 (13 pages).

United States Patent Office Action for U.S. Appl. No. 12/167,222 dated Mar. 20, 2015 (8 pages).

United States Patent Office Notice of Allowance for U.S. Appl. No. 12/167,222 dated Nov. 16, 2015 (8 pages).

* cited by examiner

FIGS. 7A-7D
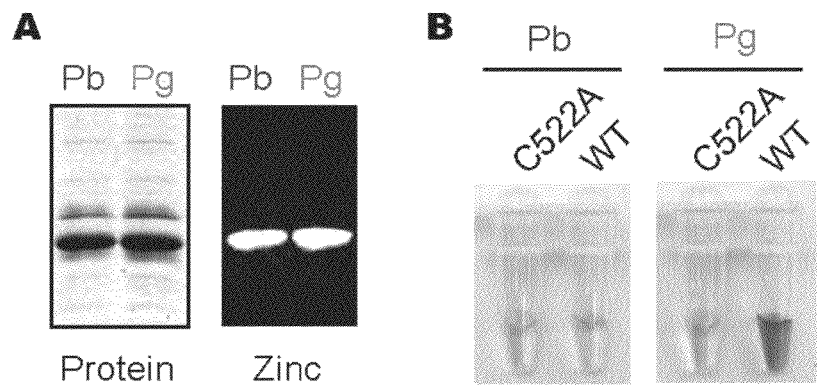
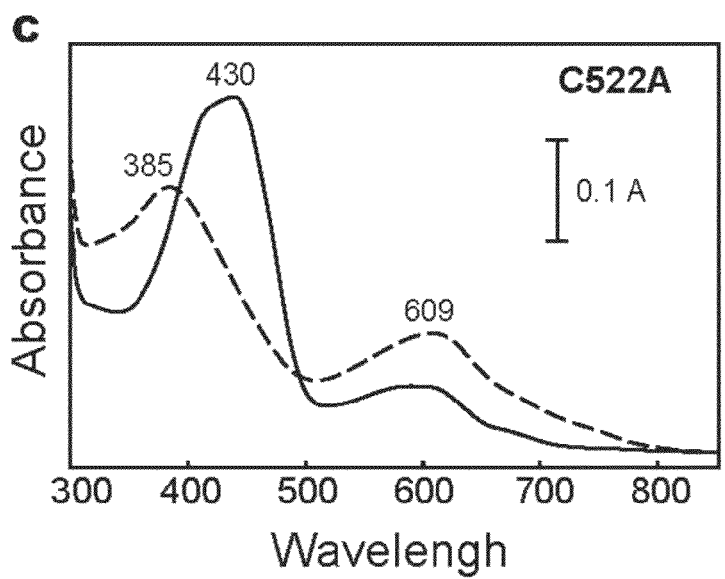
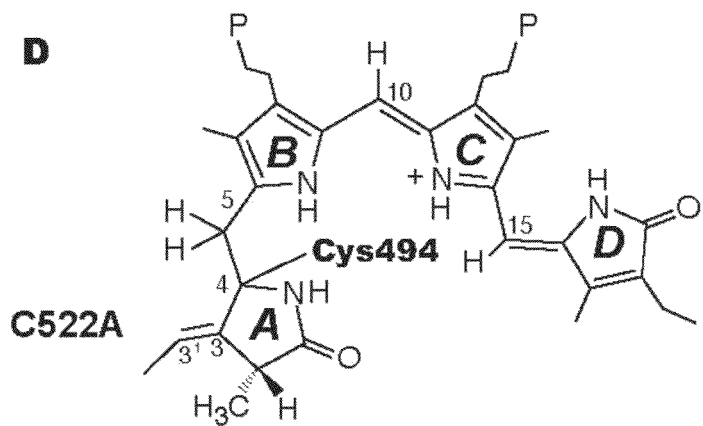

SEQUENCE LISTING

```
<160> NUMBER OF SEQ ID NOS: 49

<210> SEQ ID NO 1
<211> LENGTH: 170
<212> TYPE: PRT
<213> ORGANISM: Thermosynechococcus elongatus

<400> SEQUENCE: 1

Ala Ala Val Gln Leu Ser Glu Leu Arg Asp Arg Gln Ala Ile Phe Glu
1               5                   10                  15

Thr Leu Val Ala Lys Gly Arg Glu Leu Leu Ala Cys Asp Arg Val Ile
            20                  25                  30

Val Tyr Ala Phe Asp Asp Asn Tyr Val Gly Thr Val Val Ala Glu Ser
        35                  40                  45

Val Ala Glu Gly Trp Pro Gln Ala Arg Asp Gln Val Ile Glu Asp Pro
    50                  55                  60

Cys Phe Arg Glu His Trp Val Glu Ala Tyr Arg Gln Gly Arg Ile Gln
65                  70                  75                  80

Ala Thr Thr Asp Ile Phe Lys Ala Gly Leu Thr Glu Cys His Leu Asn
                85                  90                  95

Gln Leu Arg Pro Leu Lys Val Arg Ala Asn Leu Val Val Pro Met Val
            100                 105                 110

Ile Asp Asp Gln Leu Phe Gly Leu Leu Ile Ala His Gln Cys Ser Glu
        115                 120                 125

Pro Arg Gln Trp Gln Glu Ile Glu Ile Asp Gln Phe Ser Glu Leu Ala
    130                 135                 140

Ser Thr Gly Ser Leu Val Leu Glu Arg Leu His Phe Leu Glu Gln Thr
145                 150                 155                 160

Ile Ala Ser Leu His His His His His His
                165                 170

<210> SEQ ID NO 2
<211> LENGTH: 940
<212> TYPE: PRT
<213> ORGANISM: Thermosynechococcus elongatus
```

```
<400> SEQUENCE: 2

Met Pro Thr Met Thr Ala Lys Pro Pro Ile Asp Ile Pro Pro Leu
1               5                   10                  15

Pro Pro Ser Val Leu Asn Tyr Gln Leu Pro Ser Val Glu Glu Asn Lys
            20                  25                  30

Ala Thr Thr Asn Gly Gln Ser His Gly Gln Pro Leu Pro Thr Pro
            35                  40                  45

Pro Arg Arg Lys Phe Trp Gly Leu Arg Pro Lys Leu Ile Thr Ser Ala
    50                  55                  60

Ile Ala Leu Ala Thr Leu Pro Leu Leu Gly Val Gly Leu Val Gly Asn
65              70                  75                  80

Glu Val Val Arg Gln Asn Leu Val Gln Leu Val Leu Asp Phe Gln Gln
                85                  90                  95

Gln Gln Ala Asn Ser Val Ala Leu Gln Phe Glu Asn Tyr Leu Arg Asn
            100                 105                 110

Arg Leu Gly Asp Ala Arg Thr Leu Gly Ser Leu Leu Ser Ser Arg Tyr
            115                 120                 125

Ser Asp Lys Ile Gln Arg Arg Asp Arg Pro Gln Leu Gln Ala Ile Leu
130                 135                 140

Asp Gln Trp Leu Asn Ala Tyr Ser Asp Tyr Asp Ser Ala Gly Ile Ile
145                 150                 155                 160

Ala Asn Asp Gly Gln Gly Thr Val Ile Ala Gln Ser Ser Glu Gly Asn
                165                 170                 175

Arg Leu Ala Asn Asn Ile Leu Gln Asn Gln Gln Tyr Phe Lys Leu Ala
            180                 185                 190

Ile Gln Thr Arg Asn Pro Val Leu Thr Val Glu Pro Thr Leu Ser Leu
            195                 200                 205

Pro Asp Arg Pro Leu Gly Met Phe Leu Ala Val Pro Val Ile Asn Pro
            210                 215                 220

Gln Asn Gly Gln Ile Leu Ala Val Ala Arg Leu Arg Ile Pro Arg Ala
225                 230                 235                 240

Thr Ile Ala Glu Leu Phe Ile Thr Tyr Thr Arg Lys Gln Ser His Thr
                245                 250                 255

Phe Tyr Leu Ile Asp Ser Gly Gly Thr Ile Phe Ala Thr Thr Gln Arg
            260                 265                 270

Glu Glu Ala Ile Gln Gly Lys Pro Leu Gln Glu Val Phe Pro Lys Leu
            275                 280                 285

Ala Glu Gln Leu Gln Arg Ala Arg Ser Gly Val Ile Lys Thr Asp Ala
            290                 295                 300

Thr Phe Glu Asp Gln Ile Leu Ser Tyr Arg Gln Val Pro Ser Pro Phe
305                 310                 315                 320

Arg Ala Ile Val Leu Gly Val Asp Arg Asn Gln Ala Leu Ala Pro Leu
                325                 330                 335

Arg Thr Leu Thr Trp Thr Leu Phe Gly Gly Met Val Ile Ala Thr Gly
            340                 345                 350

Ala Val Gly Ala Ile Ala Leu Tyr Ala Thr Gln Arg Gly Leu Arg Pro
            355                 360                 365

Ile Phe Arg Thr Ile Ala Ala Val Glu Ala Ile Gly Ala Gly Asn Leu
            370                 375                 380

Asp Thr Arg Val Pro Ile Glu Thr Lys Asp Glu Leu Ala Thr Leu Gly
385                 390                 395                 400

Gln Thr Ile Asn Glu Met Val Thr Arg Leu Gln Gln Ser Phe Thr Gln
                405                 410                 415
```

```
Ile Glu Gln Ala Ala Lys Cys Ala Asp Cys Leu Arg Gln Ala Ala Val
                420                 425                 430

Gln Leu Ser Glu Leu Arg Asp Arg Gln Ala Ile Phe Glu Thr Leu Val
            435                 440                 445

Ala Lys Gly Arg Glu Leu Leu Ala Cys Asp Arg Val Ile Val Tyr Ala
        450                 455                 460

Phe Asp Asp Asn Tyr Val Gly Thr Val Val Ala Glu Ser Val Ala Glu
465                 470                 475                 480

Gly Trp Pro Gln Ala Arg Asp Gln Val Ile Glu Asp Pro Cys Phe Arg
                485                 490                 495

Glu His Trp Val Glu Ala Tyr Arg Gln Gly Arg Ile Gln Ala Thr Thr
            500                 505                 510

Asp Ile Phe Lys Ala Gly Leu Thr Glu Cys His Leu Asn Gln Leu Arg
        515                 520                 525

Pro Leu Lys Val Arg Ala Asn Leu Val Val Pro Met Val Ile Asp Asp
530                 535                 540

Gln Leu Phe Gly Leu Leu Ile Ala His Gln Cys Ser Glu Pro Arg Gln
545                 550                 555                 560

Trp Gln Glu Ile Glu Ile Asp Gln Phe Ser Glu Leu Ala Ser Thr Gly
                565                 570                 575

Ser Leu Val Leu Glu Arg Leu His Phe Leu Glu Gln Thr Ile Ala Ala
            580                 585                 590

Gln Gln Ala Ala Glu Arg Leu Ala Gln Glu Gln Gln Arg Thr Glu
        595                 600                 605

His Ile Gln Met Gln Leu Ile Lys Leu Leu Thr Glu Val Glu Ala Ala
    610                 615                 620

Ser Gln Gly Asp Leu Thr Val Arg Ala Asp Ile Thr Ala Asp Glu Ile
625                 630                 635                 640

Gly Thr Val Ala Asp Ile Phe Asn Ala Leu Ile Glu Ser Leu Arg Asp
                645                 650                 655

Val Val Val Gln Val Lys Ala Thr Thr Glu Lys Val Asn Thr Ala Leu
            660                 665                 670

Leu Ala Asp Glu Ala Ala Met Thr Glu Leu Ala Thr Glu Ser Leu Arg
        675                 680                 685

Gln Ala Lys Lys Val Lys Arg Met Leu Asp Ala Val Glu Ala Met Ala
690                 695                 700

Ser Ser Ile Glu Ser Val Ala Asn Ser Ala Asn Glu Ala Ala Ala Val
705                 710                 715                 720

Ala Arg Gln Ala Ser Glu Arg Ala Val Thr Ser Gly Glu Thr Met Asp
                725                 730                 735

Thr Thr Val Glu Ser Ile Leu Gln Leu Arg Gln Thr Val Ala Glu Thr
            740                 745                 750

Ala Lys Lys Val Lys Arg Leu Gly Glu Ser Ser Gln Ile Ser Lys
        755                 760                 765

Val Ile Ser Leu Ile Asn Gln Ile Ala Leu Gln Thr Asn Leu Leu Ala
770                 775                 780

Ile Asn Ala Ser Ile Glu Ala Ala Arg Ala Gly Glu Glu Gly Arg Gly
785                 790                 795                 800

Phe Ala Val Val Ala Glu Glu Val Gly Glu Leu Ala Ala Arg Ser Ala
                805                 810                 815

Ala Ala Thr Arg Glu Ile Glu Gln Ile Val Glu Ser Ile Gln Gln Glu
            820                 825                 830
```

```
Thr Gln Glu Val Val Ser Ala Met Glu Ala Gly Thr Ala Gln Val Val
        835                 840                 845

Glu Gly Thr Arg Leu Val Glu Ala Thr Lys Gln Ser Leu Ala Glu Ile
850                 855                 860

Val Gln Val Ser Gln His Ile Asp Glu Leu Val Gln Ser Ile Ser Gln
865                 870                 875                 880

Ala Thr Val Ser Gln Thr Arg Thr Ser Asn Thr Val Ser Thr Leu Met
                885                 890                 895

Arg Asp Phe Ala Lys Val Ser Glu Gly Met Ser Ala Thr Ser Lys Gln
            900                 905                 910

Ile Ser Glu Ser Leu Gln Ala Thr Val Asp Met Ala Gln Glu Leu Gln
        915                 920                 925

Asn Ser Val Asn Ile Phe Lys Val Thr Ala Glu Gly
    930                 935                 940

<210> SEQ ID NO 3
<211> LENGTH: 8
<212> TYPE: PRT
<213> ORGANISM: Artificial Sequence
<220> FEATURE:
<223> OTHER INFORMATION: C-terminal sequence provided by the pBAD
      protein expression vector

<400> SEQUENCE: 3

Ser Leu His His His His His His
1               5

<210> SEQ ID NO 4
<211> LENGTH: 29
<212> TYPE: DNA
<213> ORGANISM: Artificial Sequence
<220> FEATURE:
<223> OTHER INFORMATION: TePixJ GAF F1 primer

<400> SEQUENCE: 4
catggctgcg gtgcagttaa gtgagttgc                                    29

<210> SEQ ID NO 5
<211> LENGTH: 25
<212> TYPE: DNA
<213> ORGANISM: Artificial Sequence
<220> FEATURE:
<223> OTHER INFORMATION: TePixJ GAF F2 primer

<400> SEQUENCE: 5
gctgcggtgc agttaagtga gttgc                                        25

<210> SEQ ID NO 6
<211> LENGTH: 31
<212> TYPE: DNA
<213> ORGANISM: Artificial Sequence
<220> FEATURE:
<223> OTHER INFORMATION: TePixJ GAF R1 primer

<400> SEQUENCE: 6
agctggcaat ggtctgctca aggaaatgga g                                 31

<210> SEQ ID NO 7
<211> LENGTH: 27
<212> TYPE: DNA
<213> ORGANISM: Artificial Sequence
<220> FEATURE:
<223> OTHER INFORMATION: TePixJ GAF R2 primer
```

-continued

<400> SEQUENCE: 7
ggcaatggtc tgctcaagga aatggag                                27

<210> SEQ ID NO 8
<211> LENGTH: 36
<212> TYPE: DNA
<213> ORGANISM: Artificial Sequence
<220> FEATURE:
<223> OTHER INFORMATION: C522A-F primer

<400> SEQUENCE: 8
ggcagggcta acggaggctc acctgaatca actccg                      36

<210> SEQ ID NO 9
<211> LENGTH: 36
<212> TYPE: DNA
<213> ORGANISM: Artificial Sequence
<220> FEATURE:
<223> OTHER INFORMATION: C522A-R primer

<400> SEQUENCE: 9
cggagttgat tcaggtgagc ctccgttagc cctgcc                      36

<210> SEQ ID NO 10
<211> LENGTH: 40
<212> TYPE: DNA
<213> ORGANISM: Artificial Sequence
<220> FEATURE:
<223> OTHER INFORMATION: C555A-F primer

<400> SEQUENCE: 10
gtctcctgat tgcccaccag gccagtgaac cacgccagtg                  40

<210> SEQ ID NO 11
<211> LENGTH: 40
<212> TYPE: DNA
<213> ORGANISM: Artificial Sequence
<220> FEATURE:
<223> OTHER INFORMATION: C555A-R primer

<400> SEQUENCE: 11
cactggcgtg gttcactggc ctggtgggca atcaggagac                  40

<210> SEQ ID NO 12
<211> LENGTH: 41
<212> TYPE: DNA
<213> ORGANISM: Artificial Sequence
<220> FEATURE:
<223> OTHER INFORMATION: R459A-F primer

<400> SEQUENCE: 12
cgaactattg gcctgcgatg ctgtcattgt ctatgccttt g                41

<210> SEQ ID NO 13
<211> LENGTH: 41
<212> TYPE: DNA
<213> ORGANISM: Artificial Sequence
<220> FEATURE:
<223> OTHER INFORMATION: R459A-R primer

<400> SEQUENCE: 13
caaaggcata gacaatgaca gcatcgcagg ccaatagttc g                41

```
<210> SEQ ID NO 14
<211> LENGTH: 39
<212> TYPE: DNA
<213> ORGANISM: Artificial Sequence
<220> FEATURE:
<223> OTHER INFORMATION: D494N-F primer

<400> SEQUENCE: 14
ctcgagatca ggtaattgag aatccctgtt ccgcgaac                          39

<210> SEQ ID NO 15
<211> LENGTH: 39
<212> TYPE: DNA
<213> ORGANISM: Artificial Sequence
<220> FEATURE:
<223> OTHER INFORMATION: D492N-R primer

<400> SEQUENCE: 15
gttcgcggaa acagggattc tcaattacct gatctcgag                         39

<210> SEQ ID NO 16
<211> LENGTH: 39
<212> TYPE: DNA
<213> ORGANISM: Artificial Sequence
<220> FEATURE:
<223> OTHER INFORMATION: D494A-F primer

<400> SEQUENCE: 16
ctcgagatca ggtaattgag gctccctgtt ccgcgaac                          39

<210> SEQ ID NO 17
<211> LENGTH: 39
<212> TYPE: DNA
<213> ORGANISM: Artificial Sequence
<220> FEATURE:
<223> OTHER INFORMATION: D492A-R primer

<400> SEQUENCE: 17
gttcgcggaa acagggagcc tcaattacct gatctcgag                         39

<210> SEQ ID NO 18
<211> LENGTH: 39
<212> TYPE: DNA
<213> ORGANISM: Artificial Sequence
<220> FEATURE:
<223> OTHER INFORMATION: D494H-F primer

<400> SEQUENCE: 18
ctcgagatca ggtaattgag catccctgtt ccgcgaac                          39

<210> SEQ ID NO 19
<211> LENGTH: 39
<212> TYPE: DNA
<213> ORGANISM: Artificial Sequence
<220> FEATURE:
<223> OTHER INFORMATION: D492H-R primer

<400> SEQUENCE: 19
gttcgcggaa acagggatgc tcaattacct gatctcgag                         39

<210> SEQ ID NO 20
<211> LENGTH: 35
<212> TYPE: DNA
<213> ORGANISM: Artificial Sequence
<220> FEATURE:
<223> OTHER INFORMATION: Q509A-F primer
```

```
<400> SEQUENCE: 20
gccagggccg cattgcagcc acgacggata ttttc                                35

<210> SEQ ID NO 21
<211> LENGTH: 35
<212> TYPE: DNA
<213> ORGANISM: Artificial Sequence
<220> FEATURE:
<223> OTHER INFORMATION: Q509A-R primer

<400> SEQUENCE: 21
gaaaatatcc gtcgtggctg caatgcggcc ctggc                                35

<210> SEQ ID NO 22
<211> LENGTH: 33
<212> TYPE: DNA
<213> ORGANISM: Artificial Sequence
<220> FEATURE:
<223> OTHER INFORMATION: R507A-F primer

<400> SEQUENCE: 22
cctaccgcca gggcgccatt caagccacga cgg                                  33

<210> SEQ ID NO 23
<211> LENGTH: 33
<212> TYPE: DNA
<213> ORGANISM: Artificial Sequence
<220> FEATURE:
<223> OTHER INFORMATION: R507A-R primer

<400> SEQUENCE: 23
ccgtcgtggc ttgaatggcg ccctggcggt agg                                  33

<210> SEQ ID NO 24
<211> LENGTH: 44
<212> TYPE: DNA
<213> ORGANISM: Artificial Sequence
<220> FEATURE:
<223> OTHER INFORMATION: Y463H-F primer

<400> SEQUENCE: 24
ggcctgcgat cgtgtcattg tccatgcctt tgatgacaac tatg                      44

<210> SEQ ID NO 25
<211> LENGTH: 44
<212> TYPE: DNA
<213> ORGANISM: Artificial Sequence
<220> FEATURE:
<223> OTHER INFORMATION: Y463H-R primer

<400> SEQUENCE: 25
catagttgtc atcaaaggca tggacaatga cacgatcgca ggcc                      44

<210> SEQ ID NO 26
<211> LENGTH: 39
<212> TYPE: DNA
<213> ORGANISM: Artificial Sequence
<220> FEATURE:
<223> OTHER INFORMATION: D492H-F primer

<400> SEQUENCE: 26
ctcgagatca ggtaattgag catccctgtt tccgcgaac                            39
```

```
<210> SEQ ID NO 27
<211> LENGTH: 39
<212> TYPE: DNA
<213> ORGANISM: Artificial Sequence
<220> FEATURE:
<223> OTHER INFORMATION: D492H-R primer

<400> SEQUENCE: 27
gttcgcggaa acagggatgc tcaattacct gatctcgag                              39

<210> SEQ ID NO 28
<211> LENGTH: 40
<212> TYPE: DNA
<213> ORGANISM: Artificial Sequence
<220> FEATURE:
<223> OTHER INFORMATION: C494H-F primer

<400> SEQUENCE: 28
gatcaggtaa ttgaggatcc catttccgc gaacactggg                              40

<210> SEQ ID NO 29
<211> LENGTH: 40
<212> TYPE: DNA
<213> ORGANISM: Artificial Sequence
<220> FEATURE:
<223> OTHER INFORMATION: C494H-R primer

<400> SEQUENCE: 29
cccagtgttc gcggaaatgg ggatcctcaa ttacctgatc                             40

<210> SEQ ID NO 30
<211> LENGTH: 40
<212> TYPE: DNA
<213> ORGANISM: Artificial Sequence
<220> FEATURE:
<223> OTHER INFORMATION: C494A-F primer

<400> SEQUENCE: 30
gatcaggtaa ttgaggatcc cgctttccgc gaacactggg                             40

<210> SEQ ID NO 31
<211> LENGTH: 40
<212> TYPE: DNA
<213> ORGANISM: Artificial Sequence
<220> FEATURE:
<223> OTHER INFORMATION: C494A-R primer

<400> SEQUENCE: 31
cccagtgttc gcggaaagcg ggatcctcaa ttacctgatc                             40

<210> SEQ ID NO 32
<211> LENGTH: 180
<212> TYPE: PRT
<213> ORGANISM: Thermosynechococcus elongatus

<400> SEQUENCE: 32

Leu Gln Gln Ser Phe Thr Gln Ile Glu Gln Ala Ala Lys Cys Ala Asp
1               5                   10                  15

Cys Leu Arg Gln Ala Ala Val Gln Leu Ser Glu Leu Arg Asp Arg Gln
                20                  25                  30

Ala Ile Phe Glu Thr Leu Val Ala Lys Gly Arg Glu Leu Leu Ala Cys
            35                  40                  45

Asp Arg Val Ile Val Tyr Ala Phe Asp Asp Asn Tyr Val Gly Thr Val
        50                  55                  60
```

```
Val Ala Glu Ser Val Ala Glu Gly Trp Pro Gln Ala Arg Asp Gln Val
 65                  70                  75                  80

Ile Glu Asp Pro Cys Phe Arg Glu His Trp Val Glu Ala Tyr Arg Gln
                 85                  90                  95

Gly Arg Ile Gln Ala Thr Thr Asp Ile Phe Lys Ala Gly Leu Thr Glu
            100                 105                 110

Cys His Leu Asn Gln Leu Arg Pro Leu Lys Val Arg Ala Asn Leu Val
        115                 120                 125

Val Pro Met Val Ile Asp Asp Gln Leu Phe Gly Leu Leu Ile Ala His
    130                 135                 140

Gln Cys Ser Glu Pro Arg Gln Trp Gln Glu Ile Glu Ile Asp Gln Phe
145                 150                 155                 160

Ser Glu Leu Ala Ser Thr Gly Ser Leu Val Leu Glu Arg Leu His Phe
                165                 170                 175

Leu Glu Gln Thr
            180

<210> SEQ ID NO 33
<211> LENGTH: 180
<212> TYPE: PRT
<213> ORGANISM: Synechocystis sp.

<400> SEQUENCE: 33

Arg Ala Asn Leu Ile Gln Glu Arg Asn Glu Ser Ala Gln Ala Gln
 1               5                  10                  15

Ile Leu Lys Glu Leu Thr Leu Lys Ile Ser Ala Ala Ile Asn Ser Glu
                 20                  25                  30

Gln Val Phe Asp Ile Ala Ala Gln Glu Ile Arg Leu Ala Leu Lys Ala
            35                  40                  45

Asp Arg Val Ile Val Tyr Arg Phe Asp Ala Thr Trp Ala Gly Thr Val
        50                  55                  60

Ile Val Glu Ser Val Ala Glu Gly Tyr Pro Lys Ala Leu Gly Ala Thr
 65                  70                  75                  80

Ile Ala Asp Pro Cys Phe Ala Asp Ser Tyr Val Glu Lys Tyr Arg Ser
                 85                  90                  95

Gly Arg Ile Gln Ala Thr Arg Asp Ile Tyr Asn Ala Gly Leu Thr Pro
            100                 105                 110

Cys His Ile Gly Gln Leu Lys Pro Phe Glu Val Lys Ala Asn Leu Val
        115                 120                 125

Ala Pro Ile Asn Tyr Lys Gly Asn Leu Leu Gly Leu Leu Ile Ala His
    130                 135                 140

Gln Cys Ser Gly Pro Arg Asp Trp His Gln Asn Glu Ile Asp Leu Phe
145                 150                 155                 160

Gly Gln Leu Thr Val Gln Val Gly Leu Ala Leu Glu Arg Ser Asp Leu
                165                 170                 175

Leu Ala Gln Gln
            180

<210> SEQ ID NO 34
<211> LENGTH: 180
<212> TYPE: PRT
<213> ORGANISM: Cyanothece sp.
```

```
<400> SEQUENCE: 34

Arg Val Ser Leu Leu Gln Thr Gln Ile Ala Glu Asn Lys Arg Ser Gln
1               5                   10                  15

Val Leu Lys Asp Leu Val Leu Lys Leu Ile Gly Leu Ser Gln Thr His
            20                  25                  30

Ile Ile Phe Asp Thr Ala Val Glu Glu Ile Arg Gln Ala Ile Gln Cys
        35                  40                  45

Asp Arg Val Ile Ile Tyr Glu Phe Asp Glu Asn Trp Gln Gly Leu Ile
    50                  55                  60

Ile Ala Glu Ser Val Asp Glu Arg Tyr Pro Lys Ala Leu Gly Ala Ser
65                  70                  75                  80

Ile Glu Asp Pro Cys Phe Ala Glu Asn Tyr Val Asp Lys Tyr Arg Gln
                85                  90                  95

Gly Arg Val Gln Ala Thr Asp Asn Ile Tyr Asn Ala Gly Leu Thr Gln
                100                 105                 110

Cys His Leu Gln Gln Leu Glu Pro Phe Ala Val Gln Ala Asn Leu Val
            115                 120                 125

Thr Pro Ile Val Val Asn Gly Glu Leu Gly Leu Leu Ile Ala His
    130                 135                 140

His Cys Glu Ser Pro Arg His Trp Gln Pro Glu Ile Asp Phe Met
145                 150                 155                 160

Thr Gln Ala Ala Ile Gln Val Gly Val Ile Leu Glu Arg Ala Asn Leu
                165                 170                 175

Ile Gln Gln Gln
        180

<210> SEQ ID NO 35
<211> LENGTH: 180
<212> TYPE: PRT
<213> ORGANISM: Acaryochloris marina

<400> SEQUENCE: 35

Arg Ala Arg Val Met Ser His Leu Asp Ser Gln Val Asn Gln Leu Gln
1               5                   10                  15

Gln Leu Leu His Phe Thr Gln Leu Ile Arg Glu Ser Leu His Thr Glu
            20                  25                  30

Glu Ile Leu Thr Asn Ala Val Gln Glu Ser Arg Lys Val Leu Arg Ala
        35                  40                  45

Asp Arg Val Ile Val Tyr Ser Phe Asp Glu Asn Trp Gln Gly Thr Val
    50                  55                  60

Ala Ala Glu Ala Val Gln Pro Gly Ile Ser Lys Met Val Trp Ala Glu
65                  70                  75                  80

Ile Ser Asp Pro Cys Phe Ala Asn Lys Tyr Val Glu Gln Tyr Arg Arg
                85                  90                  95

Gly Arg Val Gln Ala Ile Asn Asn Val Asn Asp Ala Gly Leu Thr Glu
                100                 105                 110

Cys His Val Gln Gln Leu Glu Lys Tyr Gly Val Gln Ala Asn Leu Val
            115                 120                 125

Val Pro Ile Leu Val Gly Glu Tyr Leu Phe Gly Leu Leu Ile Ala His
    130                 135                 140

Gln Cys Ser Gly Pro Arg Ile Trp Gln Ser Ser Glu Ile Asp Leu Phe
145                 150                 155                 160
```

Thr Gln Ile Gly Val Gln Leu Gly His Ala Leu Glu Gln Ala Asn Val
                165                 170                 175

Leu Thr Gln Thr
            180

<210> SEQ ID NO 36
<211> LENGTH: 180
<212> TYPE: PRT
<213> ORGANISM: Gloeobacter violaceus

<400> SEQUENCE: 36

Arg Arg Arg Thr Glu Ala Glu Leu Gln Arg Gln Asn Arg Arg Ile Arg
1               5                   10                  15

Leu Phe Ser Asp Ile Ala Leu Lys Ile Arg Gln Ser Leu Gln Leu Glu
            20                  25                  30

Asp Ile Leu Arg Thr Ser Val Asp Glu Val Gln Lys Leu Leu Ala Ala
            35                  40                  45

Asp Arg Val Leu Ile Phe Arg Leu Trp Ala Asp Gly Thr Gly Lys Val
        50                  55                  60

Val Gln Glu Ala Val Leu Glu Ser Trp Pro Ala Ala Leu Gly Gln Asn
65                  70                  75                  80

Ile Leu Asp Pro Cys Phe Arg Asp Gly Tyr Gln Glu Gln Tyr Arg Arg
                85                  90                  95

Gly Arg Ile Gly Ala Ile Ala Asp Ile Glu Thr Ala Pro Ile Gln Pro
            100                 105                 110

Cys His Ala Asp Phe Leu Arg Arg Phe Ala Val Arg Ala Asn Leu Val
        115                 120                 125

Val Pro Ile Leu Gln Arg Glu Gln Leu Trp Gly Leu Leu Ile Ala His
130                 135                 140

Gln Cys Ser Ala Pro Arg Gln Trp Ser Thr Phe Glu Thr Glu Leu Leu
145                 150                 155                 160

Leu Gln Leu Ala Asp Gln Met Gly Ile Ala Leu Ala Gln Ala Gln Leu
                165                 170                 175

Leu Glu Gln Glu
            180

<210> SEQ ID NO 37
<211> LENGTH: 182
<212> TYPE: PRT
<213> ORGANISM: Synechocystis sp.

<400> SEQUENCE: 37

Ser Lys Glu Gln Glu Gln Arg Leu Tyr Glu Gln Gly Arg Arg Glu Ser
1               5                   10                  15

Leu Leu Arg Glu Ile Thr Gln Arg Ile Arg Gln Ser Leu Asp Leu Pro
            20                  25                  30

Thr Ile Phe Asn Thr Val Val Gln Glu Ile Arg Gln Phe Leu Glu Ala
            35                  40                  45

Asp Arg Val Val Ile Phe Gln Phe Ser Pro Asp Ser Asp Phe Ser Val
        50                  55                  60

Gly Asn Ile Val Ala Glu Ser Val Leu Ala Pro Phe Lys Pro Ile Ile
65                  70                  75                  80

Asn Ser Ala Ile Glu Glu Thr Cys Phe Ser Asn Asn Tyr Ala Gln Arg
                85                  90                  95

Tyr Gln Gln Gly Arg Ile Gln Val Ile Glu Asp Ile His Gln Ser His
            100                 105                 110

Leu Arg Gln Cys His Ile Asp Phe Leu Ala Arg Leu Gln Val Arg Ala
            115                 120                 125

Asn Leu Val Leu Pro Leu Ile Asn Asp Ala Ile Leu Trp Gly Leu Leu
        130                 135                 140

Cys Ile His Gln Cys Asp Ser Ser Arg Val Trp Glu Gln Thr Glu Ile
145                 150                 155                 160

Asp Leu Leu Lys Gln Ile Thr Asn Gln Phe Glu Ile Ala Ile Gln Gln
                165                 170                 175

Ala Thr Leu Tyr Glu Gln
            180

<210> SEQ ID NO 38
<211> LENGTH: 188
<212> TYPE: PRT
<213> ORGANISM: Thermosynechococcus elongatus

<400> SEQUENCE: 38

Gln Pro Leu Val Thr Ala Ala Leu Asn Glu Arg Gln Ala Gln Glu Arg
1               5                   10                  15

Leu Leu His Gln Val Thr Thr Gln Ile Arg Gln Ser Leu Glu Leu Pro
            20                  25                  30

Glu Leu Leu Lys Ile Ala Val Asp Arg Ile Arg Glu Phe Leu Asp Val
        35                  40                  45

Asp Arg Leu Leu Val Gly Gln Phe Ala Gln Thr Glu Gly Glu Leu Arg
    50                  55                  60

Gly Gln Ile Thr Tyr Glu Ser Cys Arg Asn Ser Glu Ile Pro Ser Val
65                  70                  75                  80

Leu Gly Ile Trp Asp Asp Cys Trp Gln Trp Ser Gly Leu Pro Ser Ser
                85                  90                  95

Ser Tyr Gln Arg Leu Ser Gln Gly Glu Ala Ile Val Val Ser Asp Ile
            100                 105                 110

Gln Gln Phe Tyr Gly Ala Val Pro Cys Leu Gln Ser Phe Ala Ala His
        115                 120                 125

Trp Gln Ile Lys Ser Trp Leu Ile Val Pro Ile Ile Val Gln Asp Arg
    130                 135                 140

Leu Trp Gly Val Leu Ile Ala His Gln Cys Asp Arg Pro Arg Gln Trp
145                 150                 155                 160

Gln Pro Gln Glu Val Glu Phe Leu Thr His Leu Ser Gln His Leu Ser
                165                 170                 175

Ile Ala Ile Tyr Gln Ala Gln Leu Tyr Ser Glu Leu
            180                 185

<210> SEQ ID NO 39
<211> LENGTH: 203
<212> TYPE: PRT
<213> ORGANISM: Synechocystis sp.

<400> SEQUENCE: 39

Ser Pro Glu Pro Ser Leu Gln Asp Ser Leu Gln Ala Ser Gln Val Lys
1               5                   10                  15

Leu Leu Ser Gln Val Ile Ala Gln Ile Arg Gln Ser Leu Asp Leu Ser
            20                  25                  30

Glu Ile Leu Asn Asn Ala Val Thr Ala Val Gln Lys Phe Leu Phe Val
        35                  40                  45

Asp Arg Leu Val Ile Tyr Gln Phe His Tyr Ser Gln Pro Ser Leu Thr
    50                  55                  60

```
Pro Leu Glu Glu Asn Gln Ile Pro Ala Pro Arg Pro Arg Gln Gln Tyr
 65                  70                  75                  80

Gly Glu Val Thr Tyr Glu Ala Arg Arg Ser Pro Glu Ile Asp Thr Met
                 85                  90                  95

Leu Gly Ile Met Thr Glu Asn Asp Cys Phe Ser Gln Val Phe Ser Tyr
            100                 105                 110

Glu Gln Lys Tyr Leu Lys Gly Ala Val Val Ala Val Ser Asp Ile Glu
        115                 120                 125

Asn His Tyr Ser Ser Ser Tyr Cys Leu Val Gly Leu Leu Gln Arg Tyr
    130                 135                 140

Gln Val Arg Ala Lys Leu Val Ala Pro Ile Ile Val Glu Gly Gln Leu
145                 150                 155                 160

Trp Gly Leu Leu Ile Ala His Gln Cys His His Pro Arg Gln Trp Leu
                165                 170                 175

Asp Ser Glu Lys Asn Phe Leu Gly Gln Ile Gly Glu His Leu Ala Val
            180                 185                 190

Ala Ile Val Gln Ser Leu Leu Tyr Ser Glu Val
            195                 200

<210> SEQ ID NO 40
<211> LENGTH: 200
<212> TYPE: PRT
<213> ORGANISM: Anabaena variabilis

<400> SEQUENCE: 40

Cys Gln Ala Val Glu Asp Ala Leu Lys Lys Gln Ile Ser Gln Glu Arg
  1               5                  10                  15

Leu Leu Asn Gln Val Thr Thr Gln Ile Arg Lys Ser Leu Asp Leu Pro
                 20                  25                  30

Val Ile Met Ala Thr Ala Ile Ala Gln Val Arg Glu Phe Leu Glu Leu
             35                  40                  45

Asp Arg Leu Val Ile Tyr Lys Phe Glu Gly Ser Gly Val Asn Thr Gln
        50                  55                  60

Asn Thr Arg Ser Pro Arg Leu Gln Asp Trp Gln Asn Tyr Gly Gly Cys
 65                  70                  75                  80

Ile Val Tyr Glu Ala Arg Ala Thr Asp Ile Ile Pro Ser Val Leu Asp
                 85                  90                  95

Tyr Gln Glu Gln Thr Cys Phe Ser Arg His Ser Gln Cys Trp Asp Lys
            100                 105                 110

Tyr Arg Gln Gly Phe Thr Leu Val Ile Asp Asp Ile Glu Thr Ala Tyr
        115                 120                 125

Ala Leu Glu Glu Cys Leu Leu Asn Phe Leu Arg Glu Ser Gln Val Arg
    130                 135                 140

Ala Lys Leu Ala Ala Pro Ile Ile Phe Glu Asp Lys Leu Trp Gly Leu
145                 150                 155                 160

Leu Ile Ala His Gln Cys Tyr Asn Pro Arg Gln Trp His Asp Ser Asp
                165                 170                 175

Lys Asn Leu Leu Ile Ser Ile Ala Glu Gln Leu Ala Ile Ala Ile His
            180                 185                 190

Gln Ser Glu Leu Met Arg Ser Leu
        195                 200

<210> SEQ ID NO 41
<211> LENGTH: 188
<212> TYPE: PRT
<213> ORGANISM: Fremyella diplosiphon
```

```
<400> SEQUENCE: 41

Arg Glu Ser Met Gln Ala Glu Leu Arg Gln Gln Gln Arg Val Glu
1               5                   10                  15

Leu Phe Ser Glu Val Thr Leu Lys Ile Arg Gln Ser Leu Gln Leu Lys
            20                  25                  30

Glu Ile Leu His Thr Thr Val Thr Glu Val Gln Arg Ile Leu Gln Ala
        35                  40                  45

Asp Arg Val Leu Ile Tyr His Val Leu Pro Asp Gly Thr Gly Lys Thr
    50                  55                  60

Ile Ser Glu Ser Val Leu Pro Asp Tyr Pro Thr Leu Met Asp Leu Glu
65                  70                  75                  80

Phe Pro Gln Glu Val Phe Pro Gln Glu Tyr Gln Gln Leu Tyr Ala Gln
                85                  90                  95

Gly Arg Val Arg Ala Ile Ala Asp Val His Asp Pro Thr Ala Gly Leu
            100                 105                 110

Ala Glu Cys Leu Val Glu Phe Val Asp Gln Phe His Ile Lys Ala Lys
        115                 120                 125

Leu Ile Val Pro Ile Val Gln Asn Leu Asn Ala Asn Ser Gln Asn Gln
    130                 135                 140

Leu Trp Gly Leu Leu Ile Ala His Gln Cys Asp Ser Val Arg Gln Trp
145                 150                 155                 160

Val Asp Phe Glu Leu Glu Leu Met Gln Gln Leu Ala Asp Gln Ile Ser
                165                 170                 175

Ile Ala Leu Ser Gln Ala Gln Leu Leu Gly Arg Leu
            180                 185

<210> SEQ ID NO 42
<211> LENGTH: 204
<212> TYPE: PRT
<213> ORGANISM: Synechococcus sp.

<400> SEQUENCE: 42

Met Asp Thr Glu Thr Trp Ala Ala Ala Arg Pro Ser Arg Asp Ala
1               5                   10                  15

Leu Ile Asn Arg Ile Thr His Gln Ile Arg Gln Ser Leu Glu Leu Asp
            20                  25                  30

Gln Ile Leu Arg Ala Thr Val Glu Glu Val Arg Ala Phe Leu Gly Thr
        35                  40                  45

Asp Arg Val Lys Val Tyr Arg Phe Asp Pro Gly His Gly Thr Val
    50                  55                  60

Val Ala Glu Ala Arg Gly Gly Glu Arg Leu Pro Ser Leu Leu Gly Leu
65                  70                  75                  80

Thr Phe Pro Ala Gly Asp Ile Pro Glu Glu Ala Arg Arg Leu Phe Arg
                85                  90                  95

Leu Ala Gln Val Arg Val Ile Val Asp Val Glu Ala Gln Ser Arg Ser
            100                 105                 110

Ile Ser Gln Pro Glu Ser Trp Gly Leu Ser Ala Arg Val Pro Leu Gly
        115                 120                 125

Glu Pro Leu Gln Arg Pro Val Asp Pro Cys His Val His Tyr Leu Lys
    130                 135                 140

Ser Met Gly Val Ala Ser Ser Leu Val Val Pro Leu Met His Gln
145                 150                 155                 160

Glu Leu Trp Gly Leu Leu Val Ser His His Ala Glu Pro Arg Pro Tyr
                165                 170                 175
```

```
Ser Gln Glu Glu Leu Gln Val Val Gln Leu Leu Ala Asp Gln Val Ser
            180                 185                 190

Ile Ala Ile Ala Gln Ala Glu Leu Leu Glu Gln Ala
        195                 200

<210> SEQ ID NO 43
<211> LENGTH: 202
<212> TYPE: PRT
<213> ORGANISM: Deinococcus radiodurans

<400> SEQUENCE: 43

Leu Glu Phe Glu Pro Thr Glu Ala Trp Asp Ser Thr Gly Pro His Ala
1               5                   10                  15

Leu Arg Asn Ala Met Phe Ala Leu Glu Ser Ala Pro Asn Leu Arg Ala
            20                  25                  30

Leu Ala Glu Val Ala Thr Gln Thr Val Arg Glu Leu Thr Gly Phe Asp
        35                  40                  45

Arg Val Met Leu Tyr Lys Phe Ala Pro Asp Ala Thr Gly Glu Val Ile
    50                  55                  60

Ala Glu Ala Arg Arg Glu Gly Leu His Ala Phe Leu Gly His Arg Phe
65                  70                  75                  80

Pro Ala Ser Asp Ile Pro Ala Gln Ala Arg Ala Leu Tyr Thr Arg His
                85                  90                  95

Leu Leu Arg Leu Thr Ala Asp Thr Arg Ala Ala Val Pro Leu Asp
            100                 105                 110

Pro Val Leu Asn Pro Gln Thr Asn Ala Pro Thr Pro Leu Gly Gly Ala
        115                 120                 125

Val Leu Arg Ala Thr Ser Pro Met His Met Gln Tyr Leu Arg Asn Met
    130                 135                 140

Gly Val Gly Ser Ser Leu Ser Val Ser Val Val Gly Gly Gln Leu
145                 150                 155                 160

Trp Gly Leu Ile Ala Cys His His Gln Thr Pro Tyr Val Leu Pro Pro
                165                 170                 175

Asp Leu Arg Thr Thr Leu Glu Tyr Leu Gly Arg Leu Leu Ser Leu Gln
            180                 185                 190

Val Gln Val Lys Glu Ala Ala Asp Val Ala
        195                 200

<210> SEQ ID NO 44
<211> LENGTH: 203
<212> TYPE: PRT
<213> ORGANISM: Synechocystis sp.

<400> SEQUENCE: 44

Glu Pro Ala Tyr Thr Ser Asp Asn Leu Pro Phe Leu Gly Phe Tyr His
1               5                   10                  15

Met Ala Asn Ala Ala Leu Asn Arg Leu Arg Gln Gln Ala Asn Leu Arg
            20                  25                  30

Asp Phe Tyr Asp Val Ile Val Glu Glu Val Arg Arg Met Thr Gly Phe
        35                  40                  45

Asp Arg Val Met Leu Tyr Arg Phe Asp Glu Asn Asn His Gly Asp Val
    50                  55                  60

Ile Ala Glu Asp Lys Arg Asp Asp Met Glu Pro Tyr Leu Gly Leu His
65                  70                  75                  80

Tyr Pro Glu Ser Asp Ile Pro Gln Pro Ala Arg Arg Leu Phe Ile His
                85                  90                  95
```

```
Asn Pro Ile Arg Val Ile Pro Asp Val Tyr Gly Val Ala Val Pro Leu
            100                 105                 110

Thr Pro Ala Val Asn Pro Ser Thr Asn Arg Ala Val Asp Leu Thr Glu
        115                 120                 125

Ser Ile Leu Arg Ser Ala Tyr His Cys His Leu Thr Tyr Leu Lys Asn
    130                 135                 140

Met Gly Val Gly Ala Ser Leu Thr Ile Ser Leu Ile Lys Asp Gly His
145                 150                 155                 160

Leu Trp Gly Leu Ile Ala Cys His His Gln Thr Pro Lys Val Ile Pro
                165                 170                 175

Phe Glu Leu Arg Lys Ala Cys Glu Phe Phe Gly Arg Val Val Phe Ser
            180                 185                 190

Asn Ile Ser Ala Gln Glu Asp Thr Glu Thr Phe
            195                 200

<210> SEQ ID NO 45
<211> LENGTH: 221
<212> TYPE: PRT
<213> ORGANISM: Arabidopsis thaliana

<400> SEQUENCE: 45

Pro Tyr Glu Val Pro Met Thr Ala Ala Gly Ala Leu Gln Ser Tyr Lys
1               5                   10                  15

Leu Ala Ala Lys Ala Ile Thr Arg Leu Gln Ser Leu Pro Ser Gly Ser
            20                  25                  30

Met Glu Arg Leu Cys Asp Thr Met Val Gln Glu Val Phe Glu Leu Thr
        35                  40                  45

Gly Tyr Asp Arg Val Met Ala Tyr Lys Phe His Glu Asp Asp His Gly
    50                  55                  60

Glu Val Val Ser Glu Val Thr Lys Pro Gly Leu Glu Pro Tyr Leu Gly
65                  70                  75                  80

Leu His Tyr Pro Ala Thr Asp Ile Pro Gln Ala Ala Arg Phe Leu Phe
                85                  90                  95

Met Lys Asn Lys Val Arg Met Ile Val Asp Cys Asn Ala Lys His Ala
            100                 105                 110

Arg Val Leu Gln Asp Glu Lys Leu Ser Phe Asp Leu Thr Leu Cys Gly
        115                 120                 125

Ser Thr Leu Arg Ala Pro His Ser Cys His Leu Gln Tyr Met Ala Asn
    130                 135                 140

Met Asp Ser Ile Ala Ser Leu Val Met Ala Val Val Val Asn Glu Glu
145                 150                 155                 160

Asp Gly Glu Gly Asp Ala Pro Asp Ala Thr Thr Gln Pro Gln Lys Arg
                165                 170                 175

Lys Arg Leu Trp Gly Leu Val Val Cys His Asn Thr Thr Pro Arg Phe
            180                 185                 190

Val Pro Phe Pro Leu Arg Tyr Ala Cys Glu Phe Leu Ala Gln Val Phe
        195                 200                 205

Ala Ile His Val Asn Lys Glu Val Glu Leu Asp Asn Gln
    210                 215                 220

<210> SEQ ID NO 46
<211> LENGTH: 4
<212> TYPE: PRT
<213> ORGANISM: Artificial Sequence
<220> FEATURE:
<223> OTHER INFORMATION: Synthetic
```

```
<400> SEQUENCE: 46

His Pro Cys Phe
1

<210> SEQ ID NO 47
<211> LENGTH: 4
<212> TYPE: PRT
<213> ORGANISM: Artificial Sequence
<220> FEATURE:
<223> OTHER INFORMATION: Synthetic

<400> SEQUENCE: 47

Ala Pro Cys Phe
1

<210> SEQ ID NO 48
<211> LENGTH: 4
<212> TYPE: PRT
<213> ORGANISM: Artificial Sequence
<220> FEATURE:
<223> OTHER INFORMATION: Synthetic

<400> SEQUENCE: 48

Asn Pro Cys Phe
1

<210> SEQ ID NO 49
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa represents Asp or Glu
<220> FEATURE:
<221> NAME/KEY: MISC_FEATURE
<222> LOCATION: (2)..(2)
<223> OTHER INFORMATION: Xaa represents Pro or Thr

<400> SEQUENCE: 49

Xaa Xaa Cys Phe
1
```

CYANOCHROME FLUOROPHORES

CROSS-REFERENCE TO RELATED APPLICATIONS

This application is a divisional of U.S. application Ser. No. 12/789,112, filed May 27, 2010, now U.S. Pat. No. 8,822,162, which claims the benefit of priority of U.S. Provisional Application No. 61/181,578, filed May 27, 2009, the entire disclosure of which is herein incorporated by reference for any purpose.

GOVERNMENT INTERESTS

This invention was made with government support under DE-FG02-88ER13968 awarded by the US Department of Energy and 0719153 awarded by the National Science Foundation. The government has certain rights in the invention.

SEQUENCE LISTING

The instant application contains a Sequence Listing which has been submitted in ASCII format via EFS-Web and is hereby incorporated by reference in its entirety. Said ASCII copy, created on Sep. 13, 2011 in Ser. No. 12/789,112, is named ASFILED_Substitute SequenceListing_CRF.txt and is 40,162 bytes in size.

FIELD OF THE INVENTION

This invention relates to new fluorescent molecules, and particularly to fluorophores with increased fluorescence and with absorbing fluorescence in the blue and green (blue/green) portion of the light spectrum.

BACKGROUND

Phytochromes (Phys) comprise a large and diverse superfamily of photoreceptors that utilize a linear tetrapyrrole bilin chromophore for light detection. Canonical Phys consist of a red-absorbing ground state (Pr) and, upon photoexcitation with red light (R), photoconvert to their often biologically active far-red light absorbing state, or Pfr (for review see Rockwell et a/., 2006, *Annu. Rev. Plant Biol.* 57: 837-858). First discovered in plants, Phys play an integral role in regulating many important aspects of the plant life cycle, such as shade avoidance, senescence, flowering time, photoperiod, and fruit ripening. These photoreceptors maintain a conserved domain architecture consisting of an N-terminal "Chromophore Binding Domain" (CBD), composed of a Per/Arndt/Sim (PAS) domain followed by a cGMP phosphodiesterase/adenyl cyclase/FhlA (GAF) domain. The CBD is tethered together by a knotted structure, whereby a conserved "lasso loop" found within the GAF domain weaves its way through the PAS domain to form a figure-of-eight configuration. The GAF domain cradles the bilin and includes the conserved cysteine (Cys)-histidine (His) motif, where an intrinsic lyase activity is responsible for forming a covalent thioether linkage to the linear tetrapyrrole phytochromobilin PΦB at the $C3^1$ carbon. This bilin drives the central event responsible for Pr to Pfr (Pr→Pfr) photoconversion by undergoing a photoisomerization of C14/15 double bond between the A and B rings of the chromophore. Immediately downstream of the CBD is the Phytochrome (PHY) domain that helps stabilize the Pfr conformation.

Although Phys were first discovered in higher plants, these receptors have since been found in lower plants, algae, fungi, cyanobacteria, and numerous probacteria. Unlike plant Phys, the cyanobacterial phytochromes (Cphs) prefer phycocyanobilin (PCB) as the chromophore that is also used as an accessory pigment for photosynthesis. PCB is synthesized in a similar manner to POB in two-step enzymatic process from heme involving a heme oxygenase and biliverdin reductase. In contrast, eubacterial Phys, or Bacterio-phytochomres (BphPs) as well as fungal phytochromes (Fphs) predominantly use biliverdin (BV) as the chromophore, made from a more simplified one-step catalyzed cleavage of heme by a heme oxygenase. In contrast to POB and PCB that form a linkage with the GAF domain, BV chromophores attach to the protein at a conserved Cys upstream of the PAS domain. Both Cph and BphP C-terminal domains have been shown to act as bona-fide HKs, whereas plant Phys appear to have diverged to acquire Ser-Thr kinase activity.

Cyanobacteria have been shown to harbor diverse members of the Phy superfamily, or Phy-like proteins, with some more divergent ones missing several key residues required for phototransformation in canonical Phys, (for reviews see Vierstra and Karniol, 2005, In: *Handbook of Photosensory Receptors*, Briggs, W. R. and Spudich, J. L., eds, Wiley-VCH Press, Weinheim, Germany, pp 171-196). One of the first of these Phy-like proteins to be described in detail, PixJ, is involved in a blue-light mediated phototaxis response in the mesophilic cyanobacterium *Synechocystis* sp. PCC6803 (Syn-PixJ; see Yoshihara et al., 2004, *Plant Cell Physiol.* 45: 1729-1737) and thermophilic cyanobacterium *Thermosynechococcus elongatus* BP-1 (TePixJ; see Ishizuka et al., 2006, *Plant Cell Physiol.* 47: 1251-1261). Renamed cyanochromes (Cycs), subsequent work has shown that these chromoproteins might harbor a less-conjugated PCB variant phycoviolobilin (PVB), contributing to their blue-shifted ground state absorbance peak absorbance of 430 nm, or Pb (Ishizuka et al., 2007, *Plant Cell Physiol.* 48: 1385-1390). Chemically identical to PCB save a missing double bond at the A-B bridge, PVB is a natural chromophore found in the phycoerythrocyanin (PEC) component of the light harvesting phycobilisomes in several cyanobacteria. Similar to PCB and POB with respect to Phys, PVB is proposed to attach to the PEC polypeptide through a $C3^1$ thioether linkage as well as undergo a Z, E photoisomerization of the C15=C16 double bond at the D-ring of the chromophore. The attachment of the bilin to PEC is assisted by two enzymes, PecE and PecF, which are responsible for the isomerization of PCB to POB and the lyase step involving the covalent attachment to the $C3^1$ Cys carbon. PVB is speculated to attach to cyanochromes in a similar manner, but through an intrinsic lyase activity similar to canonical red-absorbing Phys. However, after the proposed initial $C3^1$ thioether ligation, the events responsible for isomerization of the A-:B methine bridge of the bilin that yield the final PVB product remain enigmatic. Ishizuka et al. propose a model whereby after attachment to the $C3^1$ carbon, a basic amino acid proton donor facilitates the deconjugation of the A-B bridge (Ishizuka et al., 2007, *Plant Cell Physiol.* 48: 1385-1390).

Upon photoexcitation with blue light, cyanochromes photoconvert to a green-absorbing exited state, or Pg, which may be, in turn, reversed by subsequent green light irradiation. Unlike canonical red-absorbing Phys, cyanochromes do not require a Phy domain to undergo photoconversion to their excited state. In fact, only the GAF domain alone from TePixJ is needed for transformation to Pg. A recent report has demonstrated that a conserved Cys (TePixJ Cys-494) is actually responsible for the shift in absorbance from a red to blue absorbing chromoprotein, and that this additional Cys is required for phototransformation (Rockwell et al., 2008, *Bio-* chemistry 47: 7304-7316). This second Cys is hypothesized to covalently attach via a thioether linkage to the PCB bilin at the B-C methine bridge, and that upon blue light excitation, this transient bond is broken to yield a more conjugated green-absorbing photoproduct. However, biochemical evidence to support these claims is lacking, including hard evidence of a covalent bond provided by the second Cys to PCB. See Ulijasz et al. (2009) Journal of Biological Chemistry, Vol. 284, pp. 29757-29772.

Various methods and reporter molecules are available for monitoring gene activity and protein distribution within cells. These include the formation of fusion proteins with coding sequences for reporter molecules (markers) such as beta-galactosidase, luciferase, green fluorescent protein (GFP) and red fluorescent protein (RFP). Particularly useful reporter is GFP from the bioluminescent jellyfish *Aequorea victoria*, which is frequently used as a fluorescent marker, and is described in U.S. Pat. No. 5,491,084. However, the known reporter molecules have a variety of limitations, including short wavelength of the fluorescence emission and small separation between excitation and emission wavelength maxima. The discovery of novel reporter molecules for monitoring gene activity, protein synthesis, and protein distribution within cells, can provide very useful tools for biotechnology applications. The present invention addresses these and related needs.

BRIEF SUMMARY

Isolated polynucleotides are provided that encode modified blue/green light absorbing bacterial phytochrome domains with increased fluorescence over the corresponding wild-type bacterial phytochrome domains. The modified blue/green light absorbing bacterial phytochrome domains include *Thermosynechococcus elongatus* phytochrome domains having the Asp corresponding to position 63 of SEQ ID NO: 1 (D492) replaced with a different amino acid, such as His, Asn or Ala (D492H, D492N, or D492A), alone or in any combination with the substitutions at C494 and C555. The modified blue/green light absorbing bacterial phytochrome domains include amino acid sequences that are at least 80%, 85%, 90% or 95% identical to SEQ ID NO: 1, or positions 1 to 162 of SEQ ID NO: 1, and which may comprise one or more of the substitutions described herein. The isolated polynucleotides may encode a phytochrome domain of *Thermosynechococcus elongatus* having the Cys corresponding to position 65 of SEQ ID NO: 1 (C494) replaced with a different amino acid, such as Ala or His (C494A or C494H), alone or in any combination with the substitutions at D492 and C555. The modified phytochrome domains include those of *Thermosynechococcus elongatus* having the Cys corresponding to position 126 of SEQ ID NO: 1 (C555) replaced with a different amino acid, such as Ala (C555A).

Expression vectors are provided, which include: (a) the isolated polynucleotides described above and herein, which encode modified blue/green light absorbing bacterial phytochrome domains with increased fluorescence, and (b) regulatory sequences that are operably linked to these polynucleotides. The regulatory sequences may be promoters.

Isolated polypeptides are provided, which encode modified blue/green light absorbing bacterial phytochrome domains with increased fluorescence over the corresponding wild-type bacterial phytochrome domains. The modified blue/green light absorbing bacterial phytochrome domains include *Thermosynechococcus elongatus* phytochrome domains having the Asp corresponding to position 63 of SEQ ID NO: 1 (D492) replaced with a different amino acid, such as His, Asn or Ala (D492H, D492N, or D492A), alone or in any combination with the substitutions at C494 and C555. The isolated polypeptides include amino acid sequences that are at least 80%, 85%, 90% or 95% identical to SEQ ID NO: 1, or positions 1 to 162 of SEQ ID NO: 1, and which may comprise one or more of the substitutions described herein. The isolated polypeptides may include a phytochrome domain of *Thermosynechococcus elongatus* having the Cys corresponding to position 65 of SEQ ID NO: 1 (C494) replaced with a different amino acid, such as Ala or His (C494A or C494H), alone or in any combination with the substitutions at D492 and C555. The isolated polypeptides may further include modified phytochrome domains of *Thermosynechococcus elongatus* having the Cys corresponding to position 126 of SEQ ID NO: 1 (C555) replaced with a different amino acid, such as Ala (C555A).

Cells are provided, which include DNA molecules having regulatory elements from genes, other than genes encoding bacterial phytochromes, which regulatory elements are operably linked to DNA sequences from *Thermosynechococcus elongatus*, the DNA sequences encoding modified blue/green light absorbing bacterial phytochrome domains with increased fluorescence, where the modified bacterial phytochrome domains comprise one or more mutations of the polypeptide sequence of bacterial phytochrome which comprises an amino acid sequence that is at least 80%, 85%, 90% or 95% identical to SEQ ID NO:1, or to positions 1 to 162 of SEQ ID NO: 1, and which may comprise one or more of the substitutions described herein. In the cells, the DNA molecule having a regulatory element from a gene, other than a gene encoding a bacterial phytochrome, may be operably linked to a DNA sequence that encodes a modified *Thermosynechococcus elongatus* phytochrome domain having the Asp corresponding to position 63 of SEQ ID NO: 1 (D492) replaced with a different amino acid, such as His, Asn or Ala (D492H, D492N, or D492A), alone or in any combination with the substitutions at C494 and C555, or any polynucleotide described in the preceding paragraphs and elsewhere herein. The modified bacterial phytochrome domains may further include a phytochrome domain of *Thermosynechococcus elongatus* having the Cys corresponding to position 65 of SEQ ID NO: 1 (C494) replaced with a different amino acid, such as Ala or His (C494A or C494H), alone or in any combination with the substitutions at D492 and C555. Alternatively, or in addition, the modified bacterial phytochrome domains may further include modified phytochrome domains of *Thermosynechococcus elongatus* having the Cys corresponding to position 126 of SEQ ID NO: 1 (C555) replaced with a different amino acid, such as Ala (C555A). The cells may be selected from the group consisting of bacterial cells, yeast cells, fungal cells, plant cells, insect cells, nematode cells, animal cells, and human cells. The cells may be *Escherichia coli* cells. The regulatory elements may be promoters.

Methods for the production of modified blue/green light absorbing bacterial phytochrome domains with increased fluorescence are provided. The methods include: a) culturing cells comprising DNA molecules having regulatory elements from genes, other than genes encoding bacterial phytochromes, which are operably linked to DNA sequences from *Thermosynechococcus elongatus* encoding modified bacterial phytochrome domains with increased fluorescence; and b) isolating and purifying the modified bacterial phytochrome domains with increased fluorescence so produced by the cells. The cells may be *Escherichia coli* cells. The methods may include adding fluorescent adducts to the cells.

Methods for selecting cells that express proteins of interest are provided. The methods include: a) optionally introducing into the cells a first DNA molecule having a polynucleotide encoding the protein of interest and a second DNA molecule having a polynucleotide encoding a modified blue/green light absorbing bacterial phytochrome domain from *Thermosynechococcus elongatus* with increased fluorescence; b) culturing cells having a sequence encoding the protein of interest linked to a polynucleotide that encodes a modified blue/green light absorbing bacterial phytochrome domain with increased fluorescence over the corresponding wild-type bacterial phytochrome domain from *Thermosynechococcus elongatus* under conditions permitting expression of the modified bacterial phytochrome domain with increased fluorescence and the protein of interest; and c) selecting the cultured cells which express the modified bacterial phytochrome domain with increased fluorescence, thereby selecting cells expressing the protein of interest. The first DNA molecule and the second DNA molecule may be linked. The methods may include adding fluorescent adducts to the cells. The cells may be selected from the group consisting of bacterial cells, yeast cells, fungal cells, plant cells, insect cells, nematode cells, animal cells, and human cells. The methods may include adding fluorescent adducts to the cells.

Methods for localizing proteins of interest in cells are also provided. The methods include: a) optionally introducing into cells DNA molecules having a sequence encoding the protein of interest linked to a DNA sequence encoding a modified blue/green light absorbing bacterial phytochrome domain from *Thermosynechococcus elongatus* with increased fluorescence, such that the fusion protein produced by the cell will have the protein of interest fused to the modified bacterial phytochrome domain having increased fluorescence; b) culturing cells comprising a DNA molecule having a sequence encoding the protein of interest linked to a polynucleotide that encodes a modified blue/green light absorbing bacterial phytochrome domain with increased fluorescence over the corresponding wild-type bacterial phytochrome domain from *Thermosynechococcus elongatus*, under conditions such that a fusion protein having the protein of interest fused to the modified bacterial phytochrome domain with increased fluorescence is produced by the cell; and c) detecting the location of the fused protein, thereby localizing the proteins of interest in the cells. The methods may include adding fluorescent adducts to the cells. The cells may be selected from the group consisting of bacterial cells, yeast cells, fungal cells, plant cells, insect cells, nematode cells, animal cells, and human cells. The cells may normally express the proteins of interest. The cells may be in a living organism.

Methods for localizing a polypeptide of interest in a cell are also described in which the location of a fusion protein is determined. The fusion protein comprises the polypeptide of interest linked to one or more of the isolated modified blue/green light absorbing bacterial phytochrome domains with increased fluorescence over the corresponding wild-type bacterial phytochrome domains that are described herein. The methods may include adding fluorescent adducts to the cells. The cells may be selected from the group consisting of bacterial cells, yeast cells, fungal cells, plant cells, insect cells, nematode cells, animal cells, and human cells. The cells may normally express the proteins of interest. The cells may be in a living organism.

Methods for localizing a protein of interest in a cell also include culturing a cell comprising a DNA molecule having a sequence encoding the protein of interest linked to a DNA sequence that encodes a modified blue/green light absorbing bacterial phytochrome domain with increased fluorescence over the corresponding wild-type bacterial phytochrome domain from *Thermosynechococcus elongatus*, under conditions such that a fusion protein having the protein of interest fused to the modified bacterial phytochrome domain with increased fluorescence is produced by the cell; and detecting the location of the fused protein, thereby localizing the protein of interest in the cell. The methods may include adding fluorescent adducts to the cells. The cells may be selected from the group consisting of bacterial cells, yeast cells, fungal cells, plant cells, insect cells, nematode cells, animal cells, and human cells. The cells may normally express the proteins of interest. The cells may be in a living organism.

Methods for detecting expression of genes and regulatory nucleotide sequences in cells are provided. The methods include: a) optionally introducing into the cells DNA molecules having the gene or regulatory nucleotide sequences linked to DNA molecules or polynucleotides encoding modified blue/green light absorbing bacterial phytochrome domains from *Thermosynechococcus elongatus* having increased fluorescence, such that regulatory elements of the genes control expression of the modified bacterial phytochrome domains with increased fluorescence; b) culturing cells comprising a nucleotide molecule having the regulatory nucleotide sequence operably linked to a polynucleotide encoding a modified blue/green light absorbing bacterial phytochrome domain from *Thermosynechococcus elongatus* with increased fluorescence over the corresponding wild-type bacterial phytochrome domain, under conditions such that the regulatory nucleotide sequence directs expression of the modified bacterial phytochrome domain with increased fluorescence; and detecting the expression of the modified bacterial phytochrome domains having increased fluorescence in the cells, thereby detecting expression of the genes in the cells. The methods may include adding fluorescent adducts to the cells. The cells may be selected from the group consisting of bacterial cells, yeast cells, fungal cells, plant cells, insect cells, nematode cells, animal cells, and human cells. The cells may normally express the proteins of interest. The cells may be in a living organism.

Methods for producing fluorescent molecular weight protein markers are provided, which include: a) optionally creating DNA encoding fusion proteins, where the DNA comprises first molecules encoding modified blue/green light absorbing bacterial phytochrome domains with known molecular weight and with increased fluorescence over the corresponding wild-type bacterial phytochrome domains from *Thermosynechococcus elongatus* with second DNA molecules encoding known amino acid sequences with known molecular weight that are in the same reading frame as the first DNA molecules; b) expressing a DNA encoding a fusion protein in a protein expression system under conditions suitable to permit the expression of a fusion protein, wherein the DNA comprises a first DNA molecule encoding a modified blue/green light absorbing bacterial phytochrome domain with known molecular weight and with increased fluorescence over the corresponding wild-type bacterial phytochrome domain from *Thermosynechococcus elongatus* with a second DNA molecule encoding a known amino acid sequence with known molecular weight, wherein the first and second DNA molecules are in the same reading frame; and c) recovering the fusion proteins expressed in step (b), thereby producing fluorescent molecular weight protein markers. The methods may include expressing the fusion proteins in the presence of fluorescent molecules capable of forming fluorescent adducts with the fusion proteins. The fusion proteins may be expressed in *Escherichia coli*. The methods may further include purification of the expressed proteins.

Modified blue/green light absorbing phytochrome domains with increased fluorescence over the corresponding wild-type phytochrome domains are provided, where the wild-type phytochrome domains have an amino acid sequence comprising amino acid sequence motif Asp-Pro-Cys-Phe (positions 63 to 66 of SEQ ID NO: 1), and where the wild-type phytochrome domains have been modified to contain an amino acid other than aspartate (Asp) at position 1 of the Asp-Pro-Cys-Phe (positions 63 to 66 of SEQ ID NO: 1) sequence motif. The modified blue/green light absorbing phytochrome domains may have been modified to contain histidine, (His), asparagine (N), or alanine (Ala) instead of aspartate (Asp) at position 1 of the Asp-Pro-Cys-Phe (positions 63 to 66 of SEQ ID NO: 1) sequence motif.

BRIEF DESCRIPTION OF THE DRAWINGS

FIGS. 7A-7D shows images (FIGS. 7A, 7B), a graph (FIG. C), and a diagram (FIG. D) of the chemical structure, which illustrate how the TePixJ GAF Cys-494 thioether linkage remains after blue light irradiation.

DETAILED DESCRIPTION OF THE PRESENTLY PREFERRED EMBODIMENTS

Figure 1A:
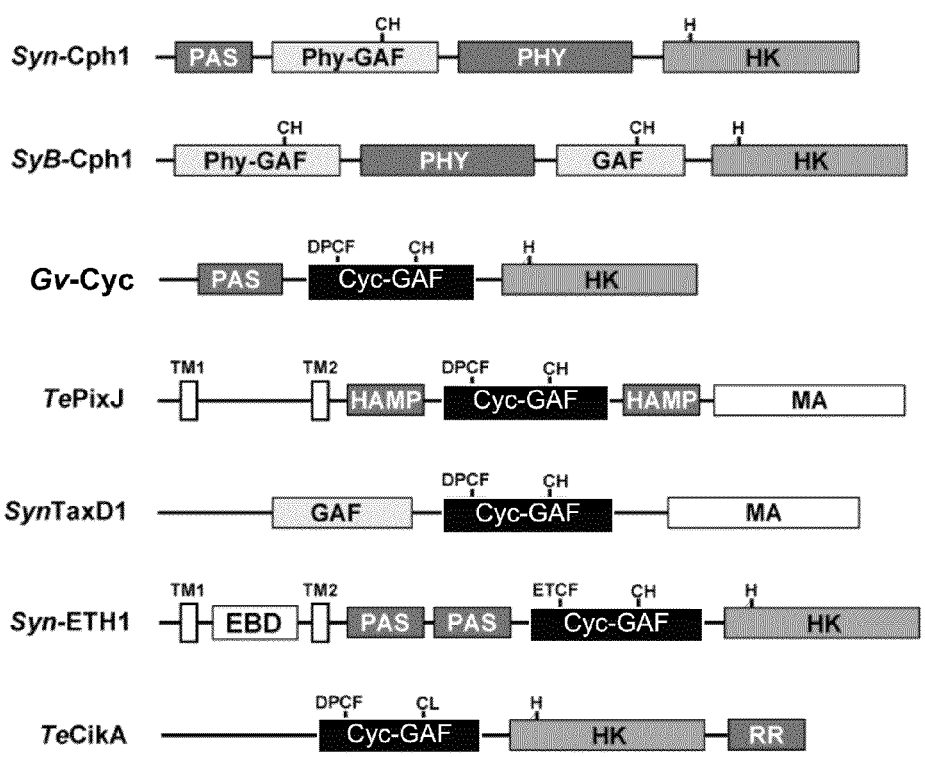
FIGS. 1A-1B shows comparative diagrams (FIG. 1A) of cyanochrome (Cyc) and phytochrome (Phy) domain architecture, and sequence alignment and secondary structure prediction (FIG. 1B).

Provided are compositions and methods that can be used as fluorescent molecules, i.e., fluorophores. Provided are modified phytochromes and modified phytochrome domains with increased fluorescence, which are suitable for use as fluorescent markers in a variety of applications. The fluorophores preferably absorb light in the blue/green part of the light spectrum, i.e. they are preferably cyanochrome fluorophores. The blue/green light absorbing phytochromes and phytochrome domains modified according to the present invention have increased fluorescence over the corresponding wild-type phytochromes and phytochrome domains.

In one aspect of the invention, provided is characterization of the cyanochrome GAF domain from the thermotolerant organism *Thermosynechococcus elongatus* BP-1 (*T. elongatus* BP-1), TePixJ, originally described by Ishizuka et al., 2006, *Plant Cell Physiol.* 47: 1251-1261. Through mutagenesis studies, important residues required for cyanochrome function are revealed. In some aspects of the invention, particular Asp-492 variants, conserved in most Phy-like proteins, yield photo-inactive chromoproteins that when irradiated with blue light produce bright green/yellow fluorescence.

In other aspects of the invention, by mutagenizing both PCB-binding cysteines, it is also shown that the second Cys, which enables the hallmark blue-shifted absorbance of cyanochromes, is indeed covalently attached to the bilin. A Cys>Ala mutation within the canonical bilin attachment CH motif (TePixJ Cys522) results in a partially photoactive protein. Resonance Raman (RR) and Infrared (IR) spectroscopy point to a linkage between the A and B rings of the chromophore that remains established throughout the photocycle. Using NMR spectroscopy it is demonstrated that that the cyanochrome bilin is protonated at all four pyrrole nitrogens in both Pb and Pg states and that only one of these N—H moieties is active during photoconversion.

In one embodiment of the invention, provided are means to create molecules with increased fluorescence from phytochromes by targeted mutation of particular amino acid residues in certain phytochrome domains. Phytochrome domains from a variety of organisms may be used as starting points for modifications that will generate the fluorochromes of the present invention. Preferably, bacterial phytochrome domains are used as starting points for modifications that will generate the fluorochromes of the present invention. "Modified phytochrome domain" means a phytochrome domain that differs from a naturally-occurring phytochrome domain by at least one amino acid. For example, mutation of the cysteine at position 494 in the DPCF (positions 63 to 66 of SEQ ID NO: 1) motif in the GAF domain of *Thermosynechococcus elongatus* to a different residue, such as alanine or histidine, results in a modified phytochrome domain. Modification of phytochromes and/or phytochrome domains can be performed by methods known in the art, e.g., by site-directed mutations, additions, deletions, and/or substitutions of one or more amino acid residues of existing phytochromes and/or phytochrome domains. Alternatively, modified phytochromes and/or phytochrome domains can be synthesized de novo, for example by synthesis of novel genes that would encode phytochrome domains with desired modifications. In certain preferred embodiments, the modified phytochrome domains of the present invention are cyanobacterial phytochrome domains, which absorb light in the blue/green part of the light spectrum.

"Fluorescence" refers to luminescence that is caused by the absorption of radiation at one wavelength followed by nearly immediate reradiation usually at a different wavelength. The fluorescence typically ceases almost at once when the incident radiation stops. The compositions of the present invention typically fluoresce red when excited with ultraviolet (UV) light, although a variety of excitation wavelengths, including the visible part of the spectrum, may be used.

"Increased fluorescence" or "enhanced fluorescence" refers to an augmented change in the level or intensity of fluorescence. Specifically, the terms "increased fluorescence" or "enhanced fluorescence" refer to the difference in the level or intensity of fluorescence between a wild-type phytochrome domain and a phytochrome domain that is modified according to the present invention. Examples of such increased fluorescence include the following: (1) the fluorescence level or intensity of the proteins modified as described herein is increased above the level of that in wild-type protein; (2) the fluorescence level or intensity of the protein modified as described herein is in an organ, tissue or cell where it is not normally detected in wild-type, non-modified controls; (3) the fluorescence level or intensity of the proteins modified as described herein is present in an organ, tissue or cell for a longer period than in wild-type controls (i.e., the duration of activity of the fluorescence of the protein is increased).

"Cyanochrome fluorophores" refers to phytochrome fluorophores that are blue/green light absorbing photoreversible phytochromes, with typical peak absorbing wavelengths at about 430 nm and 530 nm, respectively. Therefore, reference to blue/green light is meant to include the approximate blue and green portions of the light spectrum (i.e., wavelengths between about 400 nm and about 570 nm).

The usefulness of translational fusions (fusion proteins) to aid in the monitoring of expression and interaction of polypeptides has been well described. In one aspect of the invention, provided are mutations within the proposed Chromophore Binding Domain (CBD) of a blue/green photoreversible phytochrome (Phy), or a member of the cyanochrome (cyanobacteriochrome) family of photoreceptors whose natural function enables cyanobacteria to respond to blue/green light. In cyanobacteria such as *Thermosynechococcus elongatus*, similar to canonical red-absorbing phytochromes, the cyanochromes harbor a PCB-derived bilin that covalently attaches to a canonical cysteine residue (C522) located within a cGMP phosphodiesterase/adenyl cyclase/FhlA (GAF) domain. Differing from red-absorbing Phys, the cyanochrome GAF domain contains a unique (D/E)XC(F/Y) motif which is thought to be positioned near the PCB-derived chromophore based on the red-absorbing Phy structure. The cysteine (C494) found within this motif makes an additional covalent bond with the bilin that results in the cyanochrome hallmark blue-shifted absorbance.

The modified blue/green light absorbing phytochrome domains of the present invention exhibit increased fluorescence over baseline fluorescence that may be present in wild-type phytochrome domains. In some embodiments, the invention is directed to the generation of blue/green light absorbing fluorescent phytochromes from the phytochrome of *Thermosynechococcus elongatus*. The wild-type phytochrome from *Thermosynechococcus elongatus* has a DPCF motif in the GAF domain. In one embodiment of the present invention, the orange/red-fluorescing phytochrome is created by mutating the cysteine in this motif (at position 494; C494) to a different residue, such as alanine or histidine. The green/yellow-fluorescing phytochrome is created by mutating the aspartate in this domain (at position 492; D492) to a different residue, such as alanine, asparagine, or histidine. In some embodiments, the invention also comprises the mutation of a conserved solvent exposed cysteine (at position 555; C555; e.g. C555A) to prevent dimerization. Mutation of this residue assures monomeric form at >1 mM concentrations.

Preferred mutations of D492 and C494 within the DPCF motif in the GAF domain of *Thermosynechococcus elongatus* result in the emission of intense green/yellow and orange/red fluorescence with UV or orange wavelength excitation, respectfully. In this example of the invention, these two mutants may either be used separately as a fluorescent tag or together for Fluorescence Resonance Energy Transfer (FRET) applications owing to their overlapping emission and excitation fluorescent output. Such experimental results may be achieved for either in vitro or in vivo biological applications by construction of a translational fusion to the protein of choice to the blue/green absorbing fluorescent cyanochrome GAF domain, which is thermostable and only comprised of an 18 kD chromopeptide. By mutating an additional conserved, and most likely solvent exposed third cysteine residue (C555) this small GAF domain remains monomeric in solution up to concentrations exceeding 1 mM. In addition, the cyanochrome GAF domain can potentially either be expressed as apo-protein and fluorescence controlled by exogenous addition of native or synthetic fluorophores (i.e. PCB, Cy5, or derivatives thereof), or co-expressed in vivo with bilin-derivatives for detection. Applications include but are not limited to: tracking macromolecule movements in living cells by microscopy, high-throughput detection of molecules in plate-based or chip assays, detection of protein-protein interactions, and nanotechnology applications such as single-molecule measurements of biomolecular motion.

In one aspect, the invention provides at least one red and one blue fluorescent phytochrome which are small and thermostable, and which can be used in FRET as well as any application where GFP is currently used. For such applications, mutations may be introduced in different ways. In one preferred embodiment, mutations of D492 and C494 within the DPCF motif in the GAF domain of *Thermosynechococcus elongatus*, or their homologs, may be introduced on separate GAF domain molecules. In another preferred embodiment, mutations of D492 and C494 within the DPCF motif in the GAF domain of *Thermosynechococcus elongatus*, or their homologs, may be introduced on a single GAF domain molecule.

In one example, increased fluorescence resulting from modification of a phytochrome domain refers to fluorescence intensity that is at least 50% greater than the fluorescence intensity of the corresponding wild-type phytochrome domain. In other examples, increased fluorescence resulting from modification of a phytochrome domain refers to fluorescence intensity that is at least 75%, 100%, 150%, 200%, 250%, 300%, 350%, 400%, or 450% greater than the fluorescence intensity of the corresponding wild-type phytochrome domain. In a preferred embodiment, increased fluorescence resulting from modification of a phytochrome domain refers to fluorescence intensity that is 500% greater than the fluorescence intensity of the corresponding wild-type phytochrome domain.

This system not only complements but has several advantages over other more established systems (e.g. GFP and luciferase). For example, depending on a desired excitation or emission wavelength, different fluorophores can be used to "fine tune" the excitation/emission to a precise wavelength to meet the needs of a specific system or experiment, whereas other systems are limited to their inherent wavelength provided by the protein's natural chromophore (e.g. GFP and RFP). Moreover, in some embodiments, the cyanochrome blue/green and red fluorophores may also be used together to generate FRET, because their respective emission and excitation wavelengths overlap. Other advantages include a potential for N and C-terminal translational fusions or even imbedding the cyanochrome GAF domain within a desired sequence, their greatly enhanced thermostability and especially their small size (about 18 kD). Regarding the latter, it is important to note that 18 kD is smaller than both GFP (about 27 kD) and RFP (about 25.4 kD)-based tags. Although at high concentrations the protein may exist as a dimer, an optionally created mutation of a conserved solvent-exposed Cys (C555) assures monomeric form at greater than 1 mM concentrations as assayed by NMR spectroscopy.

This is a first report of genetically engineered cyanochrome fluorochromes. In contrast to the work of Rockwell et al. (2008), who described the use of the entire phytochrome full-length protein, in some embodiments of the present invention, increased fluorescence has been shown using only the GAF domain of cyanobacteriochrome.

The term "fluorescent adduct" refers to compound formed between a fluorescent molecule (i.e., one capable of absorbing light of one wavelength and emitting light of a second wavelength) and a second molecule. For example, the peptides of the present invention may contain a chromophore binding domain that may form an adduct with a fluorescent molecule (e.g., bilins).

"Apoprotein" refers to polypeptides that have a hydrophobic pocket, referred to as chromophore binding site, capable of forming a fluorescent adduct with a bilin component. The term apoprotein encompasses both naturally occurring apoproteins and variant polypeptides derived through mutagenesis. A general discussion of apoprotein structure and function is provided in Quail et al., 1997, *Plant Cell Environ.* 20: 657-665.

"Bilin" components are linear polypyrroles (for example, di-, tri-, or tetrapyrroles) capable of fluorescing when associated with an apoprotein (such as apophytochrome). The bilins may be linear bilins that are made from heme by cleaving the ring, or cyclic bilins that are heme precursors (for example protoporphyrin IX alpha or PPIXa) and heme. In some embodiments, when PPIXa binds to BphP as in the HIP mutants of BphP, the phytochrome is fluorescent. Bilin components can be isolated from plants, algae, or cyanobacteria according to standard techniques. The bilin components can also be synthesized de novo.

"Chromophore binding domain" (CBD) refers to the apoprotein N-terminal subsequence of phytochrome. Typically, the chromophore binding domain in bacterial phytochromes includes PAS and GAF domains of phytochrome. In certain cyanobacterial phytochromes such as SyA and SyB, the chromophore binding domain typically includes a GAF domain, but does not include the PAS domain.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement of other transcription control elements (e.g., enhancers) in an expression cassette. Transcriptional and translational control sequences are DNA regulatory sequences, such as promoters, enhancers, polyadenylation signals, terminators, and the like, that provide for the expression of a coding sequence in a host cell.

The terms "promoter," "promoter region," or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated nucleic acid of the present invention is separated from open reading frames that flank the desired gene and encode proteins other than the desired protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

Two nucleic acid sequences or polypeptides are said to be "identical' if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence. In the case of both expression of transgenes and inhibition of endogenous genes (e.g., by antisense or sense suppression) the inserted polynucleotide sequence need not be identical and may be "substantially identical" to a sequence of the gene from which it was derived.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

In the case where the inserted polynucleotide sequence is transcribed and translated to produce a functional polypeptide, because of codon degeneracy, a number of polynucleotide sequences will encode the same polypeptide. These variants are specifically covered by the term "polynucleotide sequence from" a particular gene. In addition, the term specifically includes sequences (e.g., full length sequences) that are substantially identical (determined as described below) with a gene sequence encoding a polypeptide of the present invention and that encode polypeptides or functional polypeptide fragments that retain the function of a polypeptide of the present invention, e.g., a modified bacterial phytochrome with increased fluorescence.

Optimal alignment of sequences for comparison may be conducted by methods commonly known in the art, for example by the search for similarity method described by Pearson and Lipman 1988, *Proc. Natl. Acad. Sci. USA* 85: 2444-2448, by computerized implementations of algorithms such as GAP, BESTFIT, BLAST, FASTA, and TFASTA in the Wisconsin Genetics Software Package, Genetics Computer Group (GCG), Madison, Wis., or by inspection. In a preferred embodiment, protein and nucleic acid sequence identities are evaluated using the Basic Local Alignment Search Tool ("BLAST), which is well known in the art (Karlin and Altschul, 1990, Proc. Natl. Acad. Sci. USA 87: 2267-2268; Altschul et al., 1997, *Nucl. Acids Res.* 25: 3389-3402), the disclosures of which are incorporated by reference in their entireties. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990). The BLAST programs can be used with the default parameters or with modified parameters provided by the user.

"Percentage of sequence identity" is determined by comparing two optimally aligned sequences over a comparison window, where the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 25% sequence identity compared to a reference sequence as determined using the programs described herein; preferably BLAST using standard parameters, as described. Alternatively, percent identity can be any integer from 25% to 100%. More preferred embodiments include polynucleotide sequences that have at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% sequence identity compared to a reference sequence. These values can be appropriately adjusted to determine corresponding identity of proteins encoded by two nucleotide sequences by taking into account codon degeneracy, amino acid similarity, reading frame positioning, and the like. Accordingly, polynucleotides of the present invention encoding a protein of the present invention include nucleic acid sequences that have substantial identity to the nucleic acid sequences that encode the polypeptides of the present invention.

The term "substantial identity" of amino acid sequences (and of polypeptides having these amino acid sequences) normally means sequence identity of at least 40% compared to a reference sequence as determined using the programs described herein; preferably BLAST using standard parameters, as described. Preferred percent identity of amino acids can be any integer from 40% to 100%. More preferred embodiments include amino acid sequences that have at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity compared to a reference sequence. Polypeptides that are "substantially identical" share amino acid sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine. Accordingly, polypeptides or proteins of the present invention include amino acid sequences that have substantial identity to the amino acid sequences of the polypeptides of the present invention, which are modified bacterial phytochromes that exhibit increased fluorescence over the corresponding wild-type bacterial phytochromes.

The invention also relates to nucleic acids that selectively hybridize to the exemplified sequences, including hybridizing to the exact complements of these sequences. The specificity of single-stranded DNA to hybridize complementary fragments is determined by the "stringency" of the reaction conditions (Sambrook et al., 1989). Hybridization stringency increases as the propensity to form DNA duplexes decreases. In nucleic acid hybridization reactions, the stringency can be chosen to favor specific hybridizations (high stringency), which can be used to identify, for example, full-length clones from a library. Less-specific hybridizations (low stringency) can be used to identify related, but not exact (homologous, but not identical), DNA molecules or segments.

DNA duplexes are stabilized by: (1) the number of complementary base pairs; (2) the type of base pairs; (3) salt concentration (ionic strength) of the reaction mixture; (4) the temperature of the reaction; and (5) the presence of certain organic solvents, such as formamide, which decrease DNA duplex stability. In general, the longer the probe, the higher the temperature required for proper annealing. A common approach is to vary the temperature; higher relative temperatures result in more stringent reaction conditions. To hybridize under "stringent conditions" describes hybridization protocols in which nucleotide sequences at least 60% homologous to each other remain hybridized. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Since the target sequences are generally present at excess, at Tm, 50% of the probes are occupied at equilibrium.

"Stringent hybridization conditions" are conditions that enable a probe, primer, or oligonucleotide to hybridize only to its target sequence (e.g., SEQ ID NO: 1, or positions 1 to 162 of SEQ ID NO: 1). Stringent conditions are sequence-dependent and will differ. Stringent conditions comprise: (1) low ionic strength and high temperature washes, for example 15 mM sodium chloride, 1.5 mM sodium citrate, 0.1% sodium dodecyl sulfate, at 50° C.; (2) a denaturing agent during hybridization, e.g. 50% (v/v) formamide, 0.1% bovine serum albumin, 0.1% Ficoll, 0.1% polyvinylpyrrolidone, 50 mM sodium phosphate buffer (750 mM sodium chloride, 75 mM sodium citrate; pH 6.5), at 42° C.; or (3) 50% formamide. Washes typically also comprise 5×SSC (0.75 M NaCl, 75 mM sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with a wash at 42° C. in 0.2×SSC (sodium chloride/sodium citrate) and 50% formamide at 55° C., followed by a high-stringency wash consisting of 0.1×SSC containing EDTA at 55° C. Preferably, the conditions are such that sequences at least about 65%, 70%, 75%, 85%, 90%, 95%, 98%, or 99% homologous to each other typically remain hybridized to each other. These conditions are presented as examples and are not meant to be limiting.

"Moderately stringent conditions" use washing solutions and hybridization conditions that are less stringent, such that a polynucleotide will hybridize to the entire, fragments, derivatives, or analogs of the target sequence (e.g., SEQ ID NO:1). One example comprises hybridization in 6×SSC, 5×Denhardt's solution, 0.5% SDS and 100 μg/ml denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions have been described (Ausubel et al., 1993; Kriegler, 1990).

"Low stringent conditions" use washing solutions and hybridization conditions that are less stringent than those for moderate stringency, such that a polynucleotide will hybridize to the entire, fragments, derivatives, or analogs. of the target sequence (e.g., SEQ ID NO: 1, or positions 1 to 162 of SEQ ID NO: 1). A non-limiting example of low stringency hybridization conditions includes hybridization in 35% formamide, 5×SSC, 50 mM Tris HCl (pH 7.5), 5 mM EDTA, 0.02% PVP, 0.02% Ficoll, 0.2% BSA, 100 μg/ml denatured salmon sperm DNA, 10% (wt/vol) dextran sulfate at 40° C., followed by one or more washes in 2×SSC, 25 mM Tris HCl (pH 7.4), 5 mM EDTA, and 0.1% SDS at 50° C. Other conditions of low stringency, such as those for cross-species hybridizations, are well-described (Ausubel et al., 1993; Kriegler, 1990).

A "functional homolog," "functional equivalent," or "functional fragment" of a polypeptide of the present invention is a polypeptide that is homologous to the specified polypeptide but has one or more amino acid differences from the specified polypeptide. A functional fragment or equivalent of a polypeptide retains at least some, if not all, of the activity of the specified polypeptide.

In one aspect, the present invention contemplates the use of a modified phytochrome as a fluorophore. In general, any phytochrome with a DPCF (Asp-Pro-Cys-Phe; positions 63 to 66 of SEQ ID NO: 1) motif may be used as to create a modified phytochrome with a variety of motifs where the DPCF motif is modified into, including but not limited to, APCF (Ala-Pro-Cys-Phe SEQ ID NO:47), NPCF (Asn-Pro-Cys-Phe; (positions 63 to 66 of SEQ ID NO: 1), or HCPF (His-Pro-Cys-Phe SEQ ID NO: 46). All of these above modified phytochromes can then be used as fluorophores with improved fluorescence. For example, various cyanobacteriochromes that have a DPCF (Asp-Pro-Cys-Phe; (positions 63 to 66 of SEQ ID NO: 1) motif may be used as starting points to create fluorophores with improved fluorescence. In one example, the present invention provides phytochromes with modified aspartate 492 (also called aspartic acid 492, Asp492, or D492) amino acid residue, which exhibit increased fluorescence. In one example, this aspartate 492 residue is located within the photochromic GAF domain of the cyanobacteriochrome from the thermophilic cyanobacterium *Thermosynechococcus elongatus*. Example of this is shown in the GAF domain from *Thermosynechococcus elongatus* BP-1 protein tll0569 (TePixJ-GAF), which is shown in SEQ ID NO: 1 at positions 1 to 162, with an SLHHHHHH (SEQ ID NO: 3) tag from position 163 to 170 of SEQ ID NO: 1. The *Thermosynechococcus elongatus* BP-1 protein tll0569 has also been described by Ishizuka et al., 2006. The amino acid sequence corresponding to the full-length amino acid sequence of the chromophore-binding domain of cyanochrome isolated from *Thermosynechococcus elongatus* is GenBank locus number tll0569, residues 1-940, and is shown as SEQ ID NO: 2.

In some embodiments of the present invention, modified phytochrome domains with increased fluorescence over the corresponding wild-type phytochrome domains are provided, where the wild-type phytochrome domains have an amino acid sequence comprising amino acid sequence motif Asp-Pro-Cys-Phe (DPCF; positions 63 to 66 of SEQ ID NO: 1), wherein the wild-type phytochrome domains have been modified to contain an amino acid other than aspartate (Asp) at position 1 of the Asp-Pro-Cys-Phe (positions 63 to 66 of SEQ ID NO: 1) sequence motif. The modified phytochrome domains may have been modified to contain histidine, (His), asparagine (N), or alanine (Ala) instead of aspartate (Asp) at position 1 of the Asp-Pro-Cys-Phe (positions 63 to 66 of SEQ ID NO: 1) sequence motif.

In one embodiment, the present invention provides modified phytochrome domains from Cyanobacteria as fluorophores with improved fluorescence. In one example, the present invention provides phytochrome D492 mutants of the cyanobacterium *Thermosynechococcus elongatus*, which exhibit increased fluorescence. The D492 residue is residue 1 in the DPCF (i.e., Asp-Pro-Cys-Phe; (positions 63 to 66 of SEQ ID NO: 1) motif. Non-limiting examples of phytochrome D492 mutants of *T. elongatus* include D492A (i.e., modification of Asp to Ala), D492H (i.e., modification of Asp to His), and D492N (i.e., modification of Asp to Asn). Functional homologs of these mutants can also be used as fluorochromes. Similar to what is described above for modifications of the cyanochrome from *T. elongatus*, it is possible to modify the corresponding aspartate in the DPCF motifs other cyanobacteria, and thus obtain fluorophores with similar fluorescence characteristics to those of the *T. elongatus* mutation. Not wanting to be bound by the following theory, this particular point mutation (D492 mutation from the DPCF motif) might have a ubiquitous effect throughout the phytochrome superfamily, which contains a DPCF (positions 63 to 66 of SEQ ID NO: 1) motif.

In another example, the present invention contemplates the use of a modified GAF domain of phytochrome as a fluorophore. The GAF domain is present in phytochromes and in cGMP-specific phosphodiesterases. The present invention contemplates the use of modified GAF domains from both phytochromes and from cGMP-specific phosphodiesterases. Various fragments of the GAF domain can be used as fluorescent molecules of the present invention. Particularly useful for practicing the present invention is the modification of the DPCF motif (i.e., Asp-Pro-Cys-Phe; positions 63 to 66 of SEQ ID NO: 1) of the *Thermosynechococcus elongatus* phytochrome, shown in amino acids 63-66 of SEQ ID NO: 1, i.e., amino acids 492-495 of SEQ ID NO:2, into an APCF (Ala-Pro-Cys-Phe; SEQ ID NO: 47), NPCF (Asn-Pro-Cys-Phe; SEQ ID NO: 48), or HCPF (His-Pro-Cys-Phe; SEQ ID NO:46) motif. It is contemplated that various modifications of this DPCF motif (and its functional equivalents in other phytochromes) will result in fluorophores useful for practicing the present invention. Some examples of fluorophores useful for the practice of this invention include modifications of the DPCF (positions 63 to 66 of SEQ ID NO: 1) motif of the GAF domain, for example: Asp to Ala (i.e., D→A); Asp to His (i.e., D→H); and Asp to Asn (i.e., D→N).

A variety of modified phytochrome domains can be used as fluorescent compositions of the present invention. In general, what is important is that the polypeptides used as fluorophores include modifications of the Asp (D) indicated above, or its equivalents in other phytochromes. In one example, preferred modifications include modifications of the DPCF motif indicated above or its equivalents in other phytochromes. The amino acid chains surrounding the one or more introduced modifications can vary in length; they can be symmetrical or asymmetrical. Thus, a variety of functional homologs of these polypeptides can be used as fluorochromes in the practice of this invention. An attenuated GAF domain from the *Thermosynechococcus elongatus* phytochrome can be modified (for example, by introducing a mutation in the GAF domain of D63 to A63, i.e. D63A; by introducing a mutation in the GAF domain of D63 to N63, i.e. D63N; or by introducing a mutation in the GAF domain of D63 to H63, i.e. D63H) and used as a fluorochrome in the practice of this invention. In general, various phytochrome GAF domains, suitably modified according to the present invention, can be used as fluorophores with increased fluorescence. Functional homologs of various GAF domains can also be modified and used as fluorochromes.

Examples of wild-type phytochrome domains that can be modified and used in the practice of this invention are shown in SEQ ID NO: 1 (amino acid sequence of the GAF domain of *Thermosynechococcus elongatus*), and in SEQ ID NO: 2 (full-length amino acid sequence of the chromophore-binding domain of cyanochrome isolated from *Thermosynechococcus elongatus*). In addition, a variety of attenuated GAF domains can be used as starting points for modifications that can generate phytochrome-based fluorochromes. Functional equivalents of these phytochrome domains can also be used as starting point for modifications, to generate fluorochromes according to this invention.

In another example, the present invention contemplates the use of a modified GAF phytochrome domain fused to the phytochrome domain PHY, as a fluorophore. The PHY domain is located at the C-terminal end of the photosensory domain (Oka et al., 2004, *Plant Cell* 16: 2104-2116). The addition of the PHY domain to the modified GAF phytochrome domain can sometimes stabilize the fluorescence of the compositions of the present invention. In examples where the GAF construct may lose the intensity of fluorescence with UV exposure, the addition of PHY can stabilize the intensity of fluorescence. If desired, additional modifications of the phytochrome domains can be performed; for example, additional amino acid residues may be added to the modified constructs, to improve the stability of the compositions of the present invention, and/or their fluorescence intensity, to minimize photobleaching, etc. As well, additional protein domains can be fused to the modified phytochrome domains.

Since the modified phytochromes of the present invention or their parallel equivalents need a fluorescent adduct to emit fluorescence, a phytofluor or an equivalent fluorescent adduct is typically provided. Fluorescent adducts such as phytofluors are known in the art (Murphy and Lagarias, 1997, *Current Biology* 7: 870-876). The fluorescent adducts are not necessarily limited to the native bilin, i.e., phycocyanobilin (PCB) for cyanobacteria Cphs and Biliverdin for Bphs, but may be any adduct which emits fluorescence as a result of binding the apoprotein (covalently or non-covalently). The fluorescent adducts are not necessarily limited to linear bilins (i.e., PCB) and can use cyclic bilins such as PPIXa. These fluorescent adducts may also be linked covalently by crosslinking techniques known in the art. The present invention contemplates fluorescent adducts consisting in some embodiments of naturally occurring or engineered apoproteins with bilins derived from different organisms, or with non-naturally occurring synthetic pyrroles.

The fluorescent adduct can be provided in a variety of ways, for example as a co-expressed entity within the system being used (e.g., coexpression of heme oxygenase with a bacterial phytochrome or BphP to make the native biliverdin chromophore), or added exogenously to the apoprotein (for example making bacterial agar plates with biliverdin in the medium to be taken into bacterial cells expressing the modified apoproteins for fluorescent bacterial colony recognition). To enable fluorescence, one or more types of fluorescent adducts may be also be added to cell culture, tissue slices, or even given to a live animal to enable the fluorescent adduct to be formed. The manner in which the fluorescent adduct is provided is irrelevant to the present invention. Alternatively, the cell or the living organism may natively provide the fluorescent adduct.

It is also important to note that the fluorescence emission wavelength may also be subject to alteration based on either further engineering the apoprotein, the use of a different fluorophore, or a combination of both. U.S. Pat. No. 6,046, 014, incorporated herein by reference, also gives several useful examples of this system, including protein-protein interactions with yeast 2-hybrid using a Phy apoprotein fusion as "bait" for a GFP-fusion as prey. The phytofluor would be added to the system to generate fluorescence energy transfer from the now fluorescent Phy to GFP to enable the detection of the interaction.

Another powerful example of how this technology can be used includes making modified (e.g. Asp492-Ala) apoprotein antibody conjugation, followed by detection by the addition of any number of phytofluors. This can also be useful in tracing protein expression in vitro, in situ, in cells, or even in a living organism. Such conjugates may be used in a number of ways to screen for interactions using a high-throughput microtiter plate assay, where the apoprotein-target fusion (e.g. Asp492→Ala) is simply detected by addition of the fluorescent adduct (phytofluor). The fluorophores may also be provided by injection (for example injection into oocytes to monitor expression of a modified (e.g. Asp492→Ala) apoprotein fusion protein).

In one aspect, this invention is particularly useful because the modified phytochromes and phytochrome domains exhibit relatively long wavelength of the fluorescence emission. In general, the novel fluorophores of this invention exhibit fluorescence in the red part of the visible light spectrum. Some of the modified phytochrome domains described herein have emission wavelengths far into the red part of the visible light spectrum, for example as far to the red part of the spectrum as 720 nm. These values exceed the examples of other fluorescent molecules with long wavelength of emission, for example mPlum, with emission max at 649 nm (Wang et a/., 2004, *Proc. Natl. Acad. Sci. USA* 101: 16745-16749; and Shaner et a/., 2004, *Nature Biotechnology* 22: 1567-1572). In addition, the modified phytochrome domains exhibit large separation between the excitation and emission wavelength maxima, which makes them particularly useful.

In another aspect, this invention contemplates the use of phytochrome fluorophores as components of fusion proteins. A "fusion protein" is a protein created through genetic engineering from two or more proteins or peptides. This is typically achieved by creating a fusion gene: removing the stop codon from the DNA sequence of the first protein, then appending the DNA sequence of the second protein in frame. The entire DNA sequence (encoding the first and the second protein) will then be expressed by a cell as a single protein (i.e., fusion protein). Optionally, one or more amino acids in the form of a linker (or "spacer") can also be added between the fused proteins or peptides. In another example, the present invention provides phytochrome C494 mutants of the cyanobacterium *Thermosynechococcus elongatus*, which exhibit increased fluorescence. The C494 residue is residue 3 in the DPCF (i.e., Asp-Pro-Cys-Phe; positions 63 to 66 of SEQ ID NO: 1) motif. Non-limiting examples of phytochrome C494 mutants of *T. elongatus* include C494A (i.e., modification of Cys to Ala), and C494H (i.e., modification of Cys to His). Functional homologs of these mutants can also be used as fluorochromes. Similar to what is described above for modifications of the cyanochrome from *T. elongatus*, it is possible to modify the corresponding cysteine in the cyanochromes of other cyanobacteria, and thus obtain fluorophores with similar fluorescence characteristics to those of the *T. elongatus* mutation. Not wanting to be bound by the following theory, this particular point mutation (C494 mutation from the DPCF motif) might have a ubiquitous effect throughout the phytochrome superfamily, which contains a DPCF or related motif.

In yet another example, the present invention provides phytochrome C555 mutants of the cyanobacterium *Thermosynechococcus elongatus*, which exhibit increased fluorescence. Non-limiting examples of phytochrome C555 mutants of *T. elongatus* include C555A (i.e., modification of Cys to Ala). Functional homologs of these mutants can also be used as fluorochromes. Similar to what is described above for modifications of the cyanochrome from *T. elongatus*, it is possible to modify the corresponding cysteine in the cyanochromes of other cyanobacteria, and thus obtain fluorophores with similar fluorescence characteristics to those of the *T.*

*elongatus* mutation. Not wanting to be bound by the following theory, this particular residue (C555) might have a ubiquitous effect throughout the phytochrome superfamily.

In some embodiments, this invention contemplates the use of a single amino acid modification for improvement of fluorescent properties of the compositions described herein. For example, a composition of the present invention may include a phytochrome domain with just a TePixJ D492 mutation as described herein. Alternatively, this invention contemplates the use of multiple amino acid modifications for improvement of fluorescent properties of the compositions described herein. For example, a composition of the present invention may include a phytochrome domain with a TePixJ D492 mutation and one or more other amino acid mutations as described herein, e.g. TePixJ C494. Additionally, or in the alternative, a composition of the present invention may include a phytochrome domain with a TePixJ D492 mutation, a TePixJ C494 mutation, and a TePixJ C555 mutation. Two or more modified phytochrome domains may be combined, for example fused into a fusion protein.

The modified phytochromes of the present invention have the potential to be expressed as apoproteins and can be detected by exogenous addition of native or synthetic fluorophores (e.g., PCB or Cy5 derivatives). Labeling of fusion proteins with synthetic fluorophores is known in the art (Keppler et al., 2004, *Proc. Natl. Acad. Sci. USA* 101: 9955-9959). Alternatively, such mutated phytochromes can be co-expressed with bilin derivatives in vivo.

Methods for detecting expression of genes in living organisms are provided. The methods include: a) introducing into cells of the living organisms DNA molecules having the gene sequences linked to DNA molecules encoding modified cyanobacterial phytochrome domains from *Thermosynechococcus elongatus* that have increased fluorescence over the corresponding wild-type cyanobacterial phytochrome domains, such that regulatory elements of the genes control expression of the modified bacterial phytochrome domains with increased fluorescence; b) culturing the cells under conditions permitting expression of the genes; and c) detecting the expression of the modified phytochrome domains with increased fluorescence in the cells, thereby detecting expression of the genes in the living organisms. The methods may include adding fluorescent adducts to the cells of the living organisms.

Methods for determining the tissue-specificity of transcription of DNA sequences in living organisms are provided. The methods include: a) introducing into cells of the living organisms first DNA molecules that include the DNA sequences that are linked to other DNA sequences encoding modified cyanobacterial phytochrome domains from *Thermosynechococcus elongatus* that have increased fluorescence over the corresponding wild-type cyanobacterial phytochrome domains, such that the first DNA sequences control expression of the modified bacterial phytochrome domains having increased fluorescence in the living organisms; and b) detecting expression of the modified bacterial phytochrome domains with increased fluorescence in different tissues of the living organisms, thereby determining the tissue-specificity of the transcription of the first DNA sequences in the living organisms. The methods may include adding fluorescent adducts to the tissues.

In contrast to other widely used fluorescent reporters (for example, Green Fluorescent Protein), which typically allow only for C-terminal protein fusions, the compositions of the present invention allow for making both C-terminal protein fusions and N-terminal protein fusions. For example, the cyanobacterial phytochrome domains from *Thermosynechococcus elongatus* lacks the N-terminal PAS domain which has been shown to prevent N-terminal fusions. Therefore, modified phytochromes according to this invention lend itself well to the creation of both C-terminal protein fusions and N-terminal fusion' proteins with improved fluorescence. The chromopeptides of the present invention are very small and may be more desirable than larger fusions when used in genetic engineering applications. In addition, in contrast to GFP, the fluorophores of the present invention do not require oxygen, which makes them particularly useful for anaerobic applications. Thus, the invention provides greater flexibility for genetically engineering protein fusions that include fluorescent reporter molecules.

The present invention contemplates the use of the fluorophore compositions and the methods for a variety of applications, including but not limited to: tracking molecule movements in living cells by microscopy; high-throughput detection of molecules in plate-based or chip assays; detection of protein-protein interactions (e.g., FRET—Fluorescence Resonance Energy Transfer); and nanotechnology applications such as single-molecule measurements of biomolecular motion. The invention is particularly useful because in some embodiments of the invention the modified phytochromes and phytochrome domains may be thermotolerant, withstanding temperatures exceeding 70° C., and thus may find utility in applications where other fluorescent reporter molecules are less useful.

It is to be understood that this invention is not limited to the particular methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

EXAMPLES

Listing of Generated TePixJ Mutants.

In some examples, the following TePixJ mutants were generated:

1) TePixJ mutant with C494A (Cys to Ala, i.e., C→A) mutation, red absorbing fluorescence (excitation wavelength=352 nm or 617 nm; emission wavelength=647 nm);

2) TePixJ mutant with C494H (Cys to His, i.e., C→H) mutation, red absorbing fluorescence (excitation wavelength=351 nm or 626 nm; emission wavelength=651 nm);

3) TePixJ mutant with D492H (Asp to His, i.e., D→H) mutation, blue/green absorbing fluorescence (excitation wavelength=552 nm; emission wavelength=578 nm);

4) TePixJ mutant with C555A (Cys to Ala, i.e., C→A) mutation, NMR indicates this is a monomer (18 kD);

5) TePixJ mutant with D492A (Asp to Ala, i.e., D→A) mutation;

6) TePixJ mutant with D492N (Asp to Asp, i.e., D→N) mutation.

TePixJ GAF Domain Alignment and Secondary Structure Prediction.

Phy/Cyc sequences were identified and extracted by performing BLAST searches of the GenBank™ database. The following GAF domain sequences were aligned using Clustal W (Thompson et al., 1994, *Nucleic Acids Res.* 22: 4673-4680): TePixJ (locus tag tll0569 from *Thermosynechococcus elongatus* BPI), SynTaxD1 (locus tag sll0041 from *Synechocystis* sp. PCC6803), Cyanothece (accession number ZP_01728273 from *Cyanothece* sp. CCY011 0), *A. mariana* (locus tag AM1_0048 from *Acaryochloris marina* MBIC11

017), G. violaceus (locus tag glr3432 from Gloeobacter violaceus PCC 7421), Syn-Etr-1 (locus tag slr1212 from Synechocystis sp. PCC6803), TeClkA (locus tag tll0899 from Thermosynechococcus elongatus BP-1), Syn-CikA (locus tag slr1969 from Synechocystis sp. PCC6803), Ana-CikA (locus tag Ava_1168 from Anabaena variabilis ATCC 29413), RcaE (accession number AAB08575 from Fremyella diplosiphon), SyB-Cph1 (locus tag CYB_2465 from Synechococcus sp. JA-23B'a(2-13)), DrBphP (locus tag DR0050 from Deinococcus radiodurans R1), Syn-Cph1 (locus tag slr0473 from Synechocystis sp. PCC6803), and At-PhyA (locus tag AT1G09570 from Arabidopsis thaliana Columbia ecotype). Alignments were displayed using MacBoxShade version 2.15 (Institute of Animal Health, Pirbright, UK): TePixJ secondary structure was predicted using the Scratch Protein Predictor (SSpro) based out of the University of California, Irvine (Pollastri et al., 2002, Proteins 47: 228-235).

Construction of Recombinant Cyc Expression Strains.

All cyanochrome sequences were amplified and cloned into NcoI/HindIII cut pBAD-6H expression plasmid using the melt and reanneal method as described (Ulijasz et al., 2008, J. Biol. Chem. 283: 21251-21266). PCR amplification of the TePixJ GAF domain (locus number tll0569, residues 430-591) was carried out using Thermosynechococcus elongatus BP-1 genomic DNA as a template. The ethylene receptor from Synechocystis sp. strain 6803 (locus number slr1212, residues 466-624) was PCR amplified from plasmid pYCDE (Rodriguez et al., 1999, Science 283: 996-998), a kind gift from Sara Patterson at the University of Wisconsin, Madison. TePixJ mutants were generated as described (Ulijasz et al., 2008) in a PCR reaction using two complementary primers containing the desired nucleotide change. Primers used in these experiments are shown in Table 1.

TABLE 1

Primers used for generation of TePixJ mutants

| TePixJ GAF domain primers | | SEQ ID NO: |
|---|---|---|
| TePixJ GAF F1) | 5'-CATGGCTGCGGTGCAGTI MGTGAGTIGC | 4 |
| TePixJ GAF F2) | 5'-GCTGCGGTGCAGTIMGTGAGTTGC | 5 |
| TePixJ GAF R1) | 5'-AGCTGGCM TGGTCTGCTCMGGAM TGGAG | 6 |
| TePixJ GAF R2) | 5'-GGCMTGGTCTGCTCMGGAMTGGAG | 7 |
| | | |
| C522A-F) | 5'-GGCAGGGCT MCGGAGGCTCACCTGM TCMCTCCG | 8 |
| C522A-R) | 5'-CGGAGTIGA TTCAGGTGAGCCTCCGTI AGCCCTGCC | 9 |
| | | |
| C555A-F) | 5'-GTCTCCTGA | 10 |
| C555A-R) | 5'-CACTGGCGTGGTICACTGGCCTGGTGGGCM TCAGGAGAC | 11 |
| | | |
| R459A-F) | 5'-CGMCTATTGGCCTGCGATGCTGTCA | 12 |
| R459A-R) | 5'-CAMGGCATAGACM TGACAGCATCGCAGGCCM TAGTICG | 13 |
| | | |
| D494N-F) | 5'-CTCGAGATCAGGT M TIGAGM TCCCTGTTICCGCGMC | 14 |
| D492N-R) | 5'-GTICGCGGAMCAGGGATTCTCM TT ACCTGATCTCGAG | 15 |
| | | |
| D494A-F) | 5'-CTCGAGATCAGGT M TIGAGGCTCCCTGTITCCGCGMC | 16 |
| D492A-R) | 5'-GTTCGCGGAMCAGGGAGCCTCM TTACCTGATCTCGAG | 17 |
| | | |
| D494H-F) | 5'-CTCGAGATCAGGTM TIGAGCATCCCTGTTTCCGCGMC | 18 |
| D492H-R) | 5'-GTICGCGGAMCAGGGATGCTCM TT ACCTGATCTCGAG | 19 |
| | | |
| Q509A-F) | 5'-GCCAGGGCCGCA TIGCAGCCACGACGGATA TITTC | 20 |
| Q509A-R) | 5'-GMM TATCCGTCGTGGCTGCM TGCGGCCCTGGC | 21 |
| | | |
| R507 A-F) | 5'-CCTACCGCCAGGGCGCCATTCMGCCACGACGG | 22 |
| R507 A-R) | 5'-CCGTCGTGGCTIGM TGGCGCCCTGGCGGTAGG | 23 |
| | | |
| Y 463H-F) | 5'- | 24 |
| Y 463H-R) | 5'-CATAGTIGTCATCAMGGCATGGACM TGACACGATCGCAGGCC | 25 |
| | | |
| D492H-F) | 5'-CTCGAGATCAGGT M TIGAGCATCCCTGTITCCGCGMC | 26 |
| D492H-R) | 5'-GTTCGCGGAMCAGGGATGCTCAA TTACCTGATCTCGAG | 27 |
| | | |
| C494H-F) | 5'-GATCAGGTM | 28 |
| C494H-R) | 5'-CCCAGTGTICGCGGAM TGGGGATCCTCM TTACCTGATC | 29 |
| | | |
| C494A-F) | 5'-GATCAGGTM | 30 |
| C494A-R) | 5'-CCCAGTGTICGCGGAMGCGGGATCCTCM TI ACCTGATC | 31 |

Protein Expression and Purification.

In general, protein expression and purification was carried out as previously described (Ulijasz et al, 2008) based on a dual plasmid expression system devised by Lagarias and Gambetta, 2001, Proc. Natl. Acad. Sci. USA 98: 10566-10571. To isotopically label the TePixJ PCB chromophore with $^{13}C$ at carbons 4, 5, 9, 10, 11, and 19, 100 mg of 5-[$^{13}C$]

α-aminolevulinic acid (ALA), a kind gift from Mario Rivera at the University of Kansas, Lawrence, Kans., was incorporated into the TePixJ polypeptide by adding it to 1 Liter (L) of the minimal expression media as described (Ulijasz et a/., 2008). Incorporation of $^{15}N$ into the TePixJ PCB chromophore was similarly accomplished by adding $C^5N$]-ALA (Medical Isotopes Inc., Pelham, N.H.) to a 1 L culture of expression media as previously described (Ulijasz et al., 2008). All samples were initially purified using nickel-chelate affinity chromatography followed by dialysis into 25 mM Tris-HCl (pH 8.0), except samples used for resonance Raman (RR) or Infrared (IR) spectroscopy, which were dialyzed into 25 mM Tris-HCl (pH 8.0) with 1 mM EDTA. Samples for NMR analysis were further purified using an FPLC purification step as described (Ulijasz et al., 2008). Fractions were then pooled and dialyzed into 10 mM Tris-DCl (pH 8.0). All dialyses were carried out using Amicon Ultra-15 centrifugal filter devices (molecular weight cut off of 10 kD; Millipore, Billerica, Mass.) with multiple spin and dilution cycles to assure samples were in the appropriate buffers without additional contaminants. For IR and RR spectroscopic studies of the 5-[$^{13}C$]-ALA labeled TePixJ sample, chromoprotein was brought to a final concentration of 1.3 mM and for NMR studies 1.75 mM. The [$^{15}N$]-ALA TePixJ sample was brought to a concentration of 1.5 mM.

Absorption and Fluorescence Spectroscopy.

Absorption spectra were measured with a PerkinElmer Lambda 650 UV/Vis Spectrometer (PerkinElmer, Waltham, Mass.) with the samples dissolved in 25 mM Tris-HCl (pH 8.0) and chromoprotein absorption peak of 0.0.0.6. Pb to Pg and Pg to Pb photoconversion was achieved with white light filtered through appropriate interference filters, 430 nm (blue filter) and 530 nm (green filter), respectfully.

Fluorescence excitation and emission spectra were recorded with a QuantaMaster Model C-60/2000 spectrofluorimeter (Photon Technologies International, Birmingham, N.J.). Emission spectra were recorded with an excitation of 523-555 nm, depending on the sample, for TePixJ wild-type, Y463H, D492H, and C522A samples, and an excitation of either 360 nm or 590 nm for the TePixJ C494H and C494A mutant samples. Excitation spectra were recorded with an excitation emission of wavelength of 551 nm to 651 nm, depending on the sample.

NMR Spectroscopy.

Isotopically-labeled forms of TePixJ (GAF) assembled with PCB (~1 mM) were dissolved in 93% $H_2O$, 7% $D_2O$, 10 mM deuterated Tris-HCl (pH 8.0), and 0.15 mM $NaN_3$ and placed in a 280 μl Shigemi microcell. $^1H$—$^{15}N$ heteronuclear single quantum coherence (HSQC) spectra $^{15}N$-labeled TePixJ (GAF) chromoprotein were collected as 128*(t1, $^{15}N$)×1022* (t2, $^1H$) data matrices. To collect an identical data set in Pg, the sample was irradiated with a white light source using a blue filter (430 nm peak bandwidth) for 30 minutes before and placed back into the same NMR magnet for data collection. Data were processed and plotted using the NMRPipe software package (Delaglio et al., 1995, *J. Biomol. NMR* 6: 277-293). All NMR data were collected at the NIH-sponsored NMR Facility at the University of Wisconsin-Madison (NMRFAM).

Cyc Domain Architecture. Sequence Alignment and Prediction of Secondary Structure.

To compare PCB-binding GAF domains from several different bacterial species and functional categories, sequences with provenance were selected and used in a NCBI Blast search to retrieve a few additional homologous, yet uncharacterized family members. As has been previously described the general domain architecture of canonical Phys is consistent, usually encompassing an N-terminal PAS domain (with the exception of PAS-less Phys), followed by a GAF, PHY, and an HK or HK-like domain. PHY and HK domains may be interrupted by additional PAS domains or another GAF domain.

FIG. 1 shows comparison of cyanochrome (Cyc) and phytochrome (Phy) domain architecture and primary sequence alignment. Domain architectures of two canonical cyanobacterial Phys, Syn-Cph1 from *Synechocystis* sp. PCC6803 and the PAS-less Phy SyB-Cph1 from *Synechococcus* sp. JA-2-3B'a are shown at top in FIG. 1A. Conversely, cyanochrome architecture is versatile, and only requires the PCB-binding GAF domain for Pb to Pg photochromicity. In support, FIG. 1A (bottom 5) show examples of the diverse domain architectures possessing cyanochrome GAF domains. These include domain sequences that are: (1) more representative of canonical Phys having a PAS-GAF-HK architecture, (2) having methyl accepting chemotaxis output domains, (3) the ethylene receptor from *Synechocystis* sp. PCC6803, and (4) several CikA homologs, or photoreceptors involved in resetting the circadian clock. As with previous descriptions of the cyanochrome family, the data suggest that this family or photoreceptors is unique to cyanobacteria.

Figure 1B:
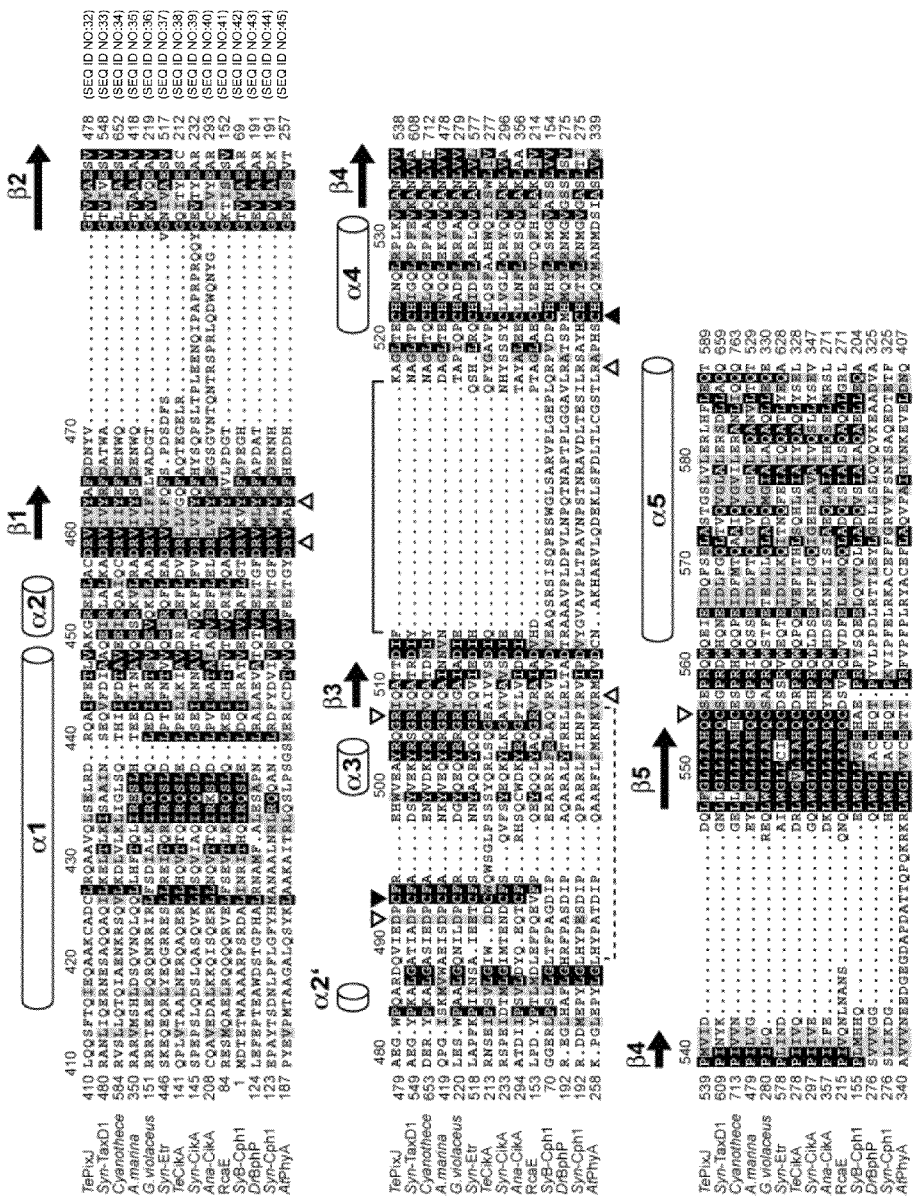

FIG. 1A: Cyc and Phy domain architecture. PAS=Per/Anrdt/Sim domain, GAF=cGMP phosphodiesterase/adenyl cyclase/FhlA domain, PHY=phytochrome domain, HK=Histidine Kinase domain, HAMP=Histidine kinase/Adenylyl cyclase/Methyl binding protein/Phosphatase domain, EBD=Ethylene binding domain, MA=Methyl-accepting chemotaxis-like domain, Phy=Phytochrome, Cyc=cyanochrome, RR=Response Regulator two-component signal transduction receiver domain. FIG. 1B: Cyc sequence alignment and secondary structure prediction. The following GAF domain sequences were aligned using Clustal W: TePixJ (locus tag tll0569 from *Thermosynechococcus elongatus* BP-1), SynTaxD1 (locus tag sll0041 from *Synechocystis* sp. PCC6803), *Cyanothece* (accession number ZP_01728273 from *Cyanothece* sp. CCY011 0), *A. mariana* (locus tag AM1_0048 from *Acaryochioris marina* MBIC11 017), *G. violaceus* (locus tag glr3432 from *Gloeobacter violaceus* PCC 7421), Syn-Etr (locus tag slr1212 from *Synechocystis* sp. PCC6803), TeClkA (locus tag tll0899 from *Thermosynechococcus elongatus* BP-1), Syn-CikA (locus tag slr1969 from *Synechocystis* sp. PCC6803), Ana-CikA (locus tag Ava_1168 from *Anabaena variabilis* ATCC 29413), RcaE (accession number AAB08575 from *Fremyella diplosiphon*), SyB-Cph1 (locus tag CYB_2465 from *Synechococcus* sp. JA-23B'a(2-13), DrBphP (locus tag DR0050 from *Deinococcus radiodurans* R1), Syn-Cph1 (locus tag slr0473 from *Synechocystis* sp. PCC6803), and At-PhyA (locus tag AT1G09570 from *Arabidopsis thaliana* Columbia ecotype). Solid triangles indicate the conserved cysteines where PCB attaches to the peptide and open circles indicate mutated residues in this study. The solid line indicates the conserved "lasso loop or knot" found in canonical Phys and absent in Cycs. The dotted line indicates a major region of sequence dissimilarity between Phys and Cycs. The predicted secondary structure of TePixJ GAF by the Scratch Protein Predictor (SSpro) based out of the University of California, Irvine is shown above the alignment. Solid horizontal arrows indicate beta-sheets and cylinders indicate alpha-helices.

To further compare diverse cyanochrome GAF domains the following sequences were obtained: TePixJ from *Thermosynechococcus elongatus* BP-1 (Ishizuka et al., 2006), TaxD1 from *Synechocystis* sp. PCC6803 (Bhaya et al., 2001, *Proc. Nat!. Acad. Sci. USA* 98: 7540-7545), ethylene receptor Etr-1 also from *Synechocystis* sp. PCC6803, and three other homologs from *Acaryochioris marina* MBIC11 017, *Gloeobacter violaceus* PCC7421, and *Cyanothece* sp. CCY0110, respectively. GAF sequences were then obtained for CikA homologs, including: the PCB-binding TeClkA from *T. elongatus* BP-1 (Schmitz et al., 2000, *Science*), CikA from *Synechocystis* sp. PCC6803 (Narikawa et al., 2008, *Photochem. Photobiol. Sci.*), and a homolog from *Anabaena variabilis* A TCC 29413. Additionally, RcaE was included, the original Phy-like protein described in bacteria involved in chromatic adaptation of the cyanobacteria *Fremyella diplosiphon* (Terauchi et al., 2004, *Mol. Microbiol.*). Lastly, four representative canonical Phys from the cyanobacteria *Synechocystis* sp. PCC6803 (Syn-Cph1, (Yeh et al., 1997, *Science*) and *Synechococcus* sp. JA-2-3B'a(2-13) (SyB-Cph1, (Ulijasz et al., 2008, *J. Biol. Chem.*), the radiotolerant eubacteria *Deinococcus radiodurans* from which a high resolution structure DrBphP has been obtained, and PhyA from the *Arabidopsis thaliana* Columbia ecotype, were included.

When aligned these sequences showed surprising similarities to the canonical red-absorbing Phys with many known functionally conserved residues (FIG. 1B). For example, all but three aligned sequences contained a conserved tyrosine residue (TePixJ residue Tyr-463) required for photoconversion in several canonical Phy variants. Importantly, all sequences possessed the conserved cysteine required for chromophore ligation (TePixJ residue Cys-522). C-terminally adjacent to this reside is a conserved His (TePixJ residue His-523), conserved in all aligned Cycs and canonical Phys but replaced by a Leu in CikA homologs, an emerging hallmark of the latter's functional role. This His residue in canonical Phys has been shown to act as a buffering system for the chromophore pocket to maintain proper photocycle chemistry and is also required for their intrinsic lyase activity. The major region of dissimilarity was a stretch of 20 amino acids that comprised a-helix 2 of the SyB-Cph1 GAF domain (FIG. 1B, dotted bracket). This helix and the preceding stretch of amino acids are conserved. among canonical Phys, coming in close contact with the bilin to form one half of the "a-helical sandwich" that cradles the chromophore. This same stretch of amino acids in Cycs, which was dubbed "the Cyc insert", contains the key residues that confer the spectroscopic differences between the red-absorbing canonical Phys and blue-absorbing Cycs (see below). Importantly, the Cyc insert contains the second cysteine (TePixJ residue Cys-494) necessary for the blue-absorbing Pb ground state and photochromicity of cyanochromes as demonstrated by Rockwell et al. The alignment presented herein shows this Cys is substituted for the conserved Asp within the "DIP" domain (FIG. 1B) required for photochromicity in canonical Phys. Cys-492 is part of a larger conserved motif (D/E-PIT-C-F; SEQ ID NO: 49) that is found in all cyanochrome GAF domains, with the Cys-Phe motif present in most all CikA homologs as well (FIG. 1B). Also worth noting is the absence of the two arginines in cyanochromes that are conserved in all red-absorbing canonical Phys (SyB-Cph1 residues R133 and R101) that stabilize Phys in the Pr and Pfr states respectively. Instead, most cyanochromes (excluding CikA homologs) possess a Gin and Ala at these sites (FIG. 1B) that suggests a different strategy is used to maintain their Pb and Pg states. Lastly, a third conserved Cys residue (TePixJ coordinate C555) was conserved in RcaE and all retrieved Cyc and CikA ortholog and homolog sequences, suggesting a possible functional significance.

To compare Cyc and canonical Phy GAF domain secondary structure, the TePixJ GAF polypeptide (residues 410-589) was entered into the Scratch Protein Predictor (SSpro). Results indicated a largely parallel structure to that of red-absorbing GAF domains, for which several 3-D structures are now available. Only a small helical region (FIG. 1B, α2', residues 484-485) was evident in the TePixJ GAF prediction that is not present in known Phy structures. A Cyc 3-D structure, however, would be required to verify this prediction.

Taken together, the observations point to a very similar overall Cyc, CikA, and Phy GAF domain topology. CikA homologs appear to be Cyc variants with subtle modifications (e.g. a "CL" substitution within the Cyc GAF "CH" and differences within the D/E-P/T-C-F (SEQ ID NO: 49) motif. These slight changes could be responsible for the observed differences in absorbance spectra and photoconversion properties in the recently characterized Syn-CikA homolog~ Thus, Cyc structure would also lend valuable insight into CikA as well as canonical red-absorbing Phy mechanisms of photoconversion.

APO-TePixJ Ligates Phycocyanobilin (PCB).

Canonical Phys have an intrinsic lyase activity that allows efficient ligation of exogenously provided chromophore to the apo-protein. This method is commonly used to incorporate either BV, as in the case of BphPs, or PCB, as in the case of cyanobacteria Phys, and can provide valuable information as to what chromophore a particular Phy superfamily member prefers. To address the question of PCB specificity for the apo-protein and whether this method could be used to incorporate high amounts of chromophore into TePixJ GAF, four one-liter cultures of *E. coli* were used to produce the TePixJ GAF apo-protein. Each one-liter culture was then harvested, lysed by sonication, and centrifuged. To the supernatants either protoporphyrin IXa, PCB, or BV were added.

Figure 2:
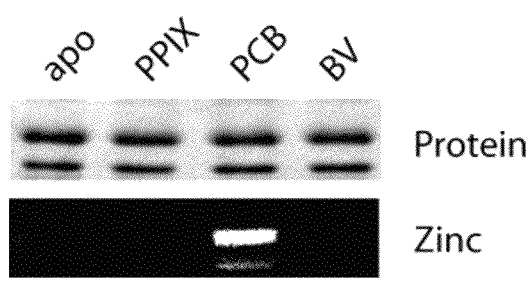
FIG. 2 shows images of SDS-PAGE gels and zinc blots illustrating how PCB binds to TePixJ.

FIG. 2 illustrates how PCB binds to TePixJ. To purified TePixJ GAF apoprotein 200 μM of protoporphyrin IXa (PPIX), biliverdin (BV), or phycocyanobilin (PCB) were added to 25 mls of a 1 L clarified cell lysate. Lysates were incubated at 4° C. for 4 hours before being purified by nickel chromatography. Purified protein was then eluted and subjected to SDS-PAGE. The gel was incubated in zinc-acetate for 5 minutes before being exposed to UV light for analysis of chromophore incorporation and subsequent Coomassie staining for protein detection. After incubation at 4° C., the protein was purified via nickel-chelate affinity chromatography. Eluted holo-protein was then subjected to SDS-PAGE and subsequent zinc-acetate and Coomassie staining. Results shown in FIG. 2 demonstrate that only PCB produced chromoprotein, as evidenced by the UV-induced zinc fluorescence. However, the amount of PCB incorporated was very low compared to in vitro assembly methods (see FIG. 3), making it difficult to assess the exact amount by UV-vis spectra analysis. Moreover, only microgram quantities apoprotein could be produced from one liter, as compared to milligram amounts of holo-protein using in vivo expression of PCB. Additionally, apo-protein was also largely susceptible to proteolytic degradation, supported by the lower molecular weight cleavage product seen in the Coomassie stained gel (FIG. 2). These data indicate that PCB is required for the TePixJ chromophore formation and that the polypeptide and holo-protein assembly need to take place in vivo for efficient chromoprotein assembly.

UV-Vis Absorbance of TePixJ Mutants.

To assess the functional importance of conserved TePixJ residues affecting photochromicity, a variety of mutants within the GAF domain polypeptide were constructed (TePixJ GAF, residues 430-591), using the wild-type GAF domain originally cloned into the pBAD-6H expression vector as a template. These mutant constructs could then be easily co-transformed with PCB-producing plasmid pL-PCB into *E*.

coli strain BL21-Al for recombinant expression followed by nickel-chelate affinity chromatography purification.

Figure 3:
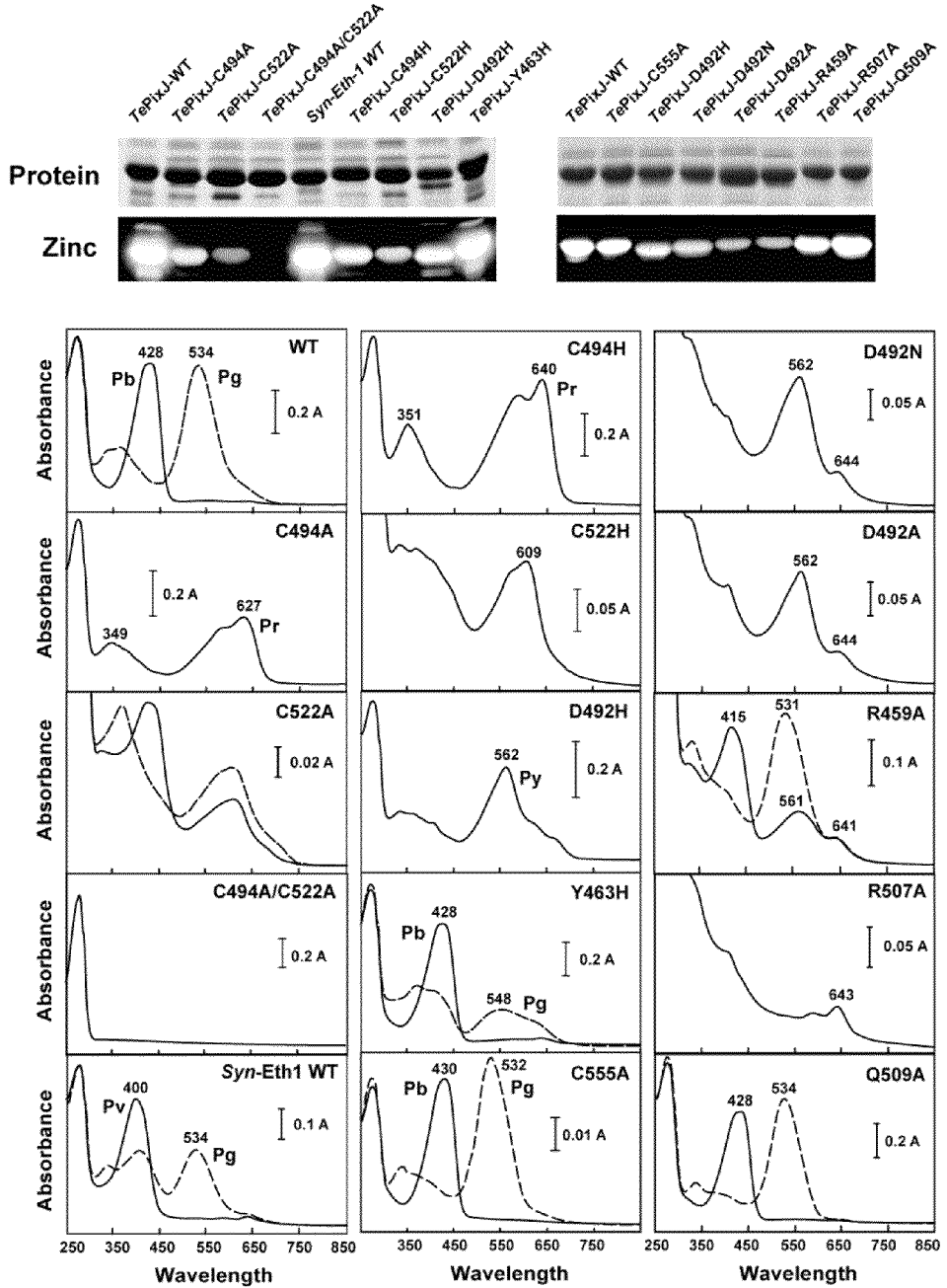
FIG. 3 shows images of SDS-PAGE gels and zinc blots (top), and graphs (bottom) illustrating the absorbance spectra of purified TePixJ GAF domain protein.

FIG. 3 shows SDS-PAGE gel, zinc blots, and absorbance spectra of purified TePixJ GAF domain protein. TePixJ (locus number tll0569 from *Thermosynechococcus elongatus* BP-1) variants and Eth-1 wild-type (locus number slr1212 from *Synechocystis* sp. strain 6803) were analyzed for purity by SDS-PAGE, chromophore (PCB) content by zinc blot, and spectral quality by absorbance spectra. Solid lines represent ground state spectra and dotted lines represent excited state spectra. Substitutions of His and Ala (this work) or Asp (Rockwell et al., 2008) at Cys494 resulted in a red-absorbing photo-inactive chromoprotein with a similar profile to SyB-Cph1 wild-type (Ulijasz et al., 2008). Both Cys522 and Cys494 mutants are still able to bind chromophore, whereas the double mutant cannot. Substitutions of His, Asn, or Ala for Asp492 resulted in a photo-inactive yellow-absorbing chromoprotein with a peak chromoprotein absorbance of 652 nm. Recombinant wild-type TePixJ GAF demonstrated high levels of expression and chromophore incorporation. Wild-type TePixJ GAF Pb and Pg absorbance spectra paralleled that of both full-length and GAF-domain-only recombinant TePixJ chromoprotein as described by Ikeuchi and colleagues (Yoshihara et al., 2004, *Plant Cell Physiol.* 45: 1729-1737) and that of full-length tlr0924 (Rockwell et al., 2008), exhibiting chromoprotein peaks of 430 nm and 530 nm, respectively. Photoconversion of TePixJ-GAF to Pg exhibited no evidence of dark reversion when monitored by both UV-vis and NMR spectroscopy (data not shown).

To confirm that the Cyc variant used (TePixJ, locus number tll0569) produced a similar phenotype to that of the Cyc described by Rockwell et al., 2008 (locus number tlr0924, an Ala substitution was introduced in the equivalent TePixJ Cys residue (C494A). As shown in FIG. 3, this mutant incorporated PCB and exhibited an almost identical absorbance spectrum to that of tlr0924 C499D, paralleling that of a canonical red-absorbing Phy Pr ground state. Interestingly, the peak absorbance of the chromoprotein (627 nm) was blue shifted from that of Cph1 (659 nm), baring more similarity to the SyB-Cph1 Pr UV-vis profile (Pr peak absorbance 630 nm, suggesting a similar chromophore geometry. Also paralleling the tlr0924 C499D mutant, TePixJ C494A was photoinactive. A C494H variant yielded an almost identical PCB incorporation and UV-vis profile (FIG. 3).

To demonstrate that Cys-494 forms a covalent bond with the TePixJ chromophore, both single C522A and double C552NC494A mutants were also constructed and purified protein assessed for bilin incorporation by zinc blot analysis. If Cys-494 was indeed covalently attached to the bilin, it may be possible to eliminate the canonical Cys-522 thioether linkage site (FIG. 1B) while still retaining the second Cys-494/PCB covalent bond. Although not as bright as the wild-type, the zinc blot shown in FIG. 3 (left) showed clear UV-induced fluorescence with both C522A and C522H variants in comparison to the double C552NC494A mutant, demonstrating that Cys-494 is indeed covalently attached to the bilin and that removal of both Cys-522 and Cys-494 abrogates all detectable chromophore binding. UV-vis spectral analysis of the C494A variant (FIG. 3) produced two ground state peaks, a major peak of 430 nm, similar to wild-type Pg, as well as a smaller one at 606 nm. When irradiated with blue light (430 nm), the major peak shifted into the UV (370 nm) and was accompanied by an increase in the 606 orange peak. The C522H substitution was able to incorporate slightly more chromophore than the C522A variant, but was completely photo-inactive (data not shown). For this mutant the 430 peak was not observed, replaced by a broadened or bleached signal in the same area of the spectrum (FIG. 3). Collectively these mutants demonstrate that PCB is covalently bound to the GAF domain pocket with both Cys-522 and Cys-494, with Cys-494 being the weaker of the two linkages based on zinc blot assessment of chromophore incorporation (FIG. 3). In addition alanine was introduced at Cys555, which is conserved in all Cyc, RcaE, and CikA homologs. Based on alignments with known Phy GAF structures, Cys-555 is predicted to be solvent exposed and not within range of the chromophore binding pocket (data not shown). This mutant proved to be especially useful for NMR analysis based on its HSQC $^1$H—$^{15}$N 20 spectra (see below). As shown in FIG. 3, the TePixJ-GAF C555A variant exhibited indistinguishable Pb/Pg spectra from that of wild-type.

Also within the conserved D/E-P/T-C-F (SEQ ID NO: 49) motif is Asp-492 (TePixJ coordinate), another residue that is highly conserved and unique to Cycs. Because the Asp found within the invariant canonical Phy family "DIP" motif is intimately involved in Phy photochromicity and is thought to be a possible proton acceptor during the Pr to Pfr photocycle, Asp-492 might hold a similar function in Cycs. As a result, this residue was mutated to an Ala, Asp, and His for recombinant protein expression and spectroscopic analysis.

Zinc blots shown in FIG. 3 demonstrate that all three Asp-492 variants could express well in *E. coli* and bind PCB. The amount of chromophore bound varied depending on the mutation, with the D492H variant able to incorporate the most. UV-vis spectroscopic analysis shown in FIG. 3 revealed a similar absorbance profile for all three mutants, exhibiting one major chromoprotein peak in the yellow portion of the visible spectrum at 562 nm with a shoulder at 325 nm. This absorbance profile was similar to that of denatured wild-type TePixJ and reconstituted PecA-31-Cys-PVB. All three Asp-492 variants were photochemically locked and showed no appreciated ability to photoconvert to a different species (data not shown). These data show that Asp-492 is required to attain the observed wild-type TePixJ Pb chromoprotein peak of 430 and preserve photochromicity.

In many Cyc sequences, the Asp-492 position is occupied by the other acidic amino acid, glutamic acid. For example, the GAF domain found within the *Synechocystis* ethylene receptor (locus slr1212) has an ETCF motif in place of the "DPCF" sequence (FIG. 1). To demonstrate that natural variation in Cyc receptors can accommodate another similar amino acid in this same position to allow a fully photochromic chromopeptide, this GAF domain was cloned, expressed recombinantly as described herein, and purified for biochemical and spectroscopic characterization. FIG. 3 demonstrates that the *Synechocystis* ethylene receptor GAF domain polypeptide (Etr-1, residues 466-624) expressed well and could accommodate large amounts of PCB bilin as determined by zinc blot analysis (FIG. 3, left panel). The dark-adapted state of Etr-1 was blue-shifted by 30 nm relative to that of Asp-containing Cyc family members, yielding a violet peak absorbance of 400 nm (Pv) just on the cusp of the visible spectrum (FIG. 3). When irradiated with blue/violet light a distinct Pg state was observed paralleling that of other Cycs (peak absorbance 530 nm). These data suggest that a glutamic acid at this position suffices to allow photoconversion to occur, and that variations within the conserved DPCF motif could result in different bilin-protein interactions to modify PCB absorbance properties.

As evidenced in the alignment shown in FIG. 1B, other conserved residues necessary for proper canonical Phy function are different in Cycs. Most notably, the two arginines required for Pr and Pfr stability in canonical Phys, SyBCph1 coordinates Arg-133 and Arg-101 respectively, were absent in Cycs, including the chromatic adaptation Phy-like protein RcaE and circadian entrainment CikA receptors (FIG. 1B). In Cycs Arg-133 generally appears as an alanine (TePixJ coordinate A518) and Arg-101 a glutamine (TePixJ coordinate 0509), suggesting an alternative bilin-binding domain. A 0509A mutant exhibited wild-type Pb and Pg absorbances and ligated ample amounts of PCB (FIG. 3). Since the 0509A mutant did not effect cyanochrome photochromicity, nearby Arg507, which is conserved in Cycs but absent in other Phy variants (FIG. 1B), was investigated for a potential role. A R508A mutant bound PCB well and exhibited a similar dark adapted absorbance spectrum to D492 variants, except no peak was observed at 562 nm. Also paralleling that of D492 mutants, the R507A chromoprotein was photo-inactive. These data suggest that Arg-507 is not required for chromophore ligation but contributes substantially to wild-type absorbance and by association, cyanochrome photochromicity.

Lastly, mutations were introduced into two highly conserved residues, Asp-459 (D459A) and Tyr-463 (Y463H). These amino acids are conserved in most all Phys, with the TePixJ Tyr-463 equivalent necessary for Pr to Pfr photoconversion in most canonical red-absorbing versions, but not all. The TePixJ-GAF Y 463H mutant was able to both assemble chromoprotein and produce a Pb spectrum similar to that of wild-type (FIG. 3). After blue-light irradiation a bleached green-absorbing photoproduct was observed, which was unable to be converted back to Pb with green light irradiation (FIG. 3 and data not shown). These data indicate that Y463 is important for Pb to Pg photoconversion, paralleling results of canonical Phys.

The conserved Arg-459 (TePixJ coordinate) has never been mutated within the Phy superfamily. FIG. 3 indicates that a PixJ-GAF R459A variant could assemble with PCB, but in lower quantities than wild-type or other mutants (FIG. 3, right panel). Absorbance spectra indicated a dark-adapted major absorbance peak of 415 nm, with additional peaks at 561 nm and 641 nm, the latter two similar to that of D492 variants. Surprisingly, when irradiated with blue light, these peaks converged to give a single wild-type absorbance Pg peak at 531 nm (FIG. 3). When exposed to green light the ground state spectrum was only partially restored. From these data one might infer that Asp-459 is partially responsible for stabilizing the Pb state, but is not necessary for Pb to Pg photoconversion and stabilization of the Pg photoproduct.

Fluorescence of TePixJ Mutants.

Most all Phy family members inherently emit low levels of fluorescence when irradiated with the appropriate wavelength of light, which may be substantially enhanced by mutagenesis of certain residues involved in photoconversion. To date, data point to a parallel correlation between lack of photoconversion and fluorescence intensity. Such mutant Phys that emit fluorescence have been gaining potential for use as biological markers. As FIG. 3 illustrates, substitutions within the TePixJ-GAF chromopeptide at positions Asp-492 and Cys-494 resulted in a complete abrogation of photoconversion and yielded a yellow (562 nm) and red (628 nm) UV-vis chromoprotein absorption peaks, respectively. To investigate the fluorescence potential of these and other mutants, fluorescence emission and excitation spectra were measured using a scanning fluorometer as described (Ulijasz et al., 2008, *J. Biol. Chem.*).

Figure 4:
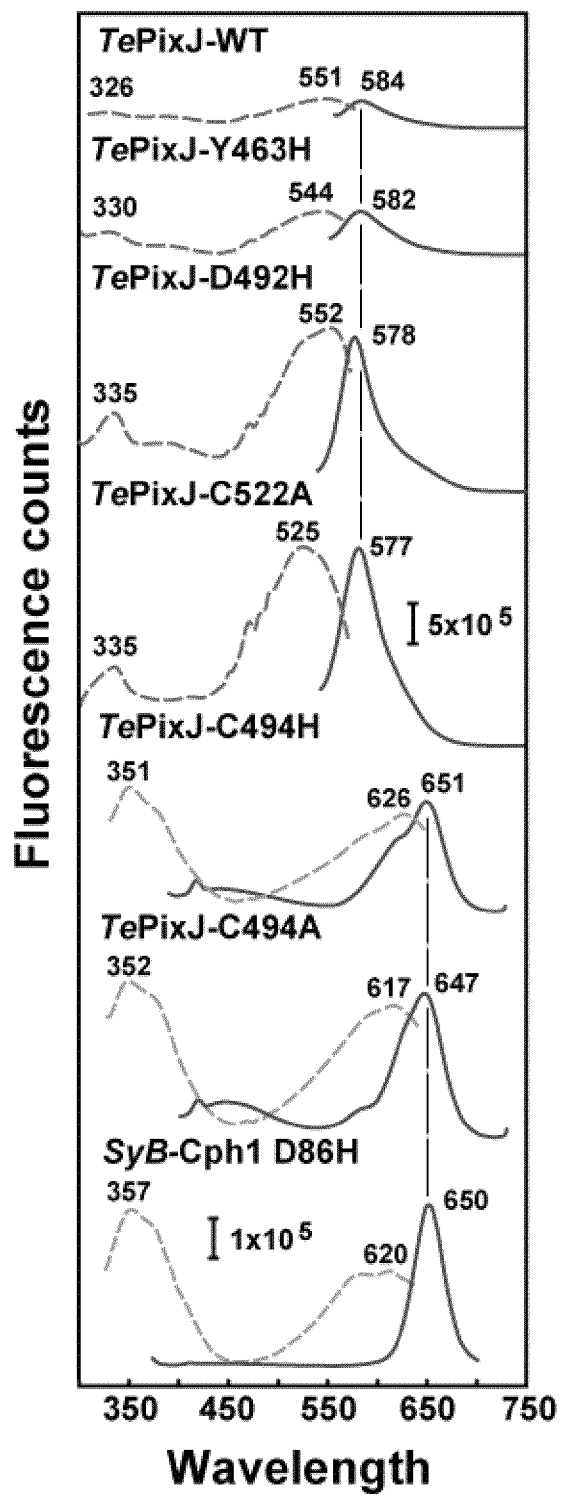
FIG. 4 shows graphs illustrating how amino acid substitutions in TePixJ GAF result in fluorescent chromoprotein.

To observe color absorbance under white light and initially test for UV-induced fluorescence, equal amounts of purified TePixJ-GAF chromoprotein were distributed into strip tubes and examined under ambient (white) light and a UV light box. FIG. 4 illustrates how amino acid substitutions in TePixJ GAF at C494 and D494 result in fluorescent chromoprotein. FIG. 4 shows scanning fluorescence spectroscopy of a set of TePixJ variants compared to the strongly red fluorescent SyB-Cph1 D86H mutant (Ulijasz et a/., 2008). Substitutions at the D492 position result in intense red fluorescence, whereas mutations at the C492 position result in intense red fluorescence (peak emission=647 nm). Note that the TePixJ C492 mutants give a peak emission close to that of the SyB-Cph1 D86H variant (peak emission=650 nm). Dotted lines=excitation spectra and solid lines=emission spectra.

Results depicted in FIG. 4 show, as expected, wild-type TePixJ is a yellowish color under white light, exhibiting very little UV-induced fluorescence. Scanning fluorescence revealed small and large excitation peaks of 326 nm and 551 nm, respectively, with a single emission peak at 584 nm (FIG. 4). TePixJ-GAF Y463H, C555A, and Q509A showed a similar yellow color and fluorescence intensities to that of wild-type samples, with the Y 463H variant giving parallel emission and excitation peaks. Although TePixJ C522A incorporated only a small amount of PCB, when normalized for chromoprotein and measured for fluorescence intensity an approximate 8-fold increase over that of wild-type was observed. C522A excitation and emission peaks paralleled that of wild-type (FIG. 4). The double C522A1C494A mutant produced no pigmented color or fluorescence.

Several mutated residues diverged greatly from wild-type in both fluorescence intensity and emission/excitation peaks. For example, all Asp-492 variants (D492A, D492N, and D492H) were purple in color and all exhibited fluorescence when irradiated with UV-light. TePixJ-GAF D492H, which incorporated the most PCB of the three Asp-492 mutants (FIG. 3), was further analyzed with scanning fluorescence. Results indicated similar excitation and emission spectra to wild-type, but with a 6-fold increase in fluorescence counts (FIG. 4). Similar to Cys-499 in tlr0942, initial assessment of TePixJ mutants C492A and C494H were highly fluorescent and produced a deep blue colored protein resembling that of SyB-Cph1 wild-type. Scanning fluorescence of both mutants resulted in emission spectra almost identical to that of SyB-Cph1 D86H, with peaks at 351-352 nm and 626-617 nm (FIG. 4). Finally, TePixJ-GAF R459A purified chromoprotein maintained a brownish-red color and exhibited fluorescence under UV light. Excitation and emission spectra were not determined for this mutant.

In summary, all three mutations that displayed a marked increase in levels of UV-induced fluorescence (Asp-492, Cys-494, Cys-522, and Arg-459) were also deficient in photoconversion (FIG. 3), paralleling results of mutations in canonical red-absorbing Phys. TePixJ-GAF variants in residues that yielded either a wild-type or a distinct photoproduct were generally less fluorescent (Tyr463, Cys-555, Arg-507, and Gln-509; compare FIG. 3 and FIG. 4). These data point to a general correlation between abrogation of photoconversion and fluorescence in photoactive linear tetrapyrrole binding GAF domains.

NMR Analysis of TePixJ PCB in Pg and Pb States.

Previously the inventors were able to selectively isotopically label the SyB-Cph1 PCB chromophore with $^{15}N$ or $^{13}C$ (Ulijasz et al., 2008). One-dimensional and two-dimensional NMR data gave us valuable information as to the solvent and conformational exchange of the pyrrole nitrogens and methyl groups in both Pr and Pfr conformers. This technology was ultimately used to collect three-dimensional NMR data whereby the chromophore of SyB-Cph1 GAF could be tethered to the protein through NOE restraints. To determine the activity of selected TePixJ-GAF PCB atoms in both Pg and Pb states, a similar labeling scheme was used. $[^{15}N]$-ALA and 5-[$^{13}$C]-ALA were used to selectively label all four pyrrole nitrogens with $^{15}$N, and the A-B, B-C, and C-D methine bridges (PCB carbons C5, C10 and C15) as well as four other carbons (C4, C9, C11 and C19), respectively.

Figure 5:
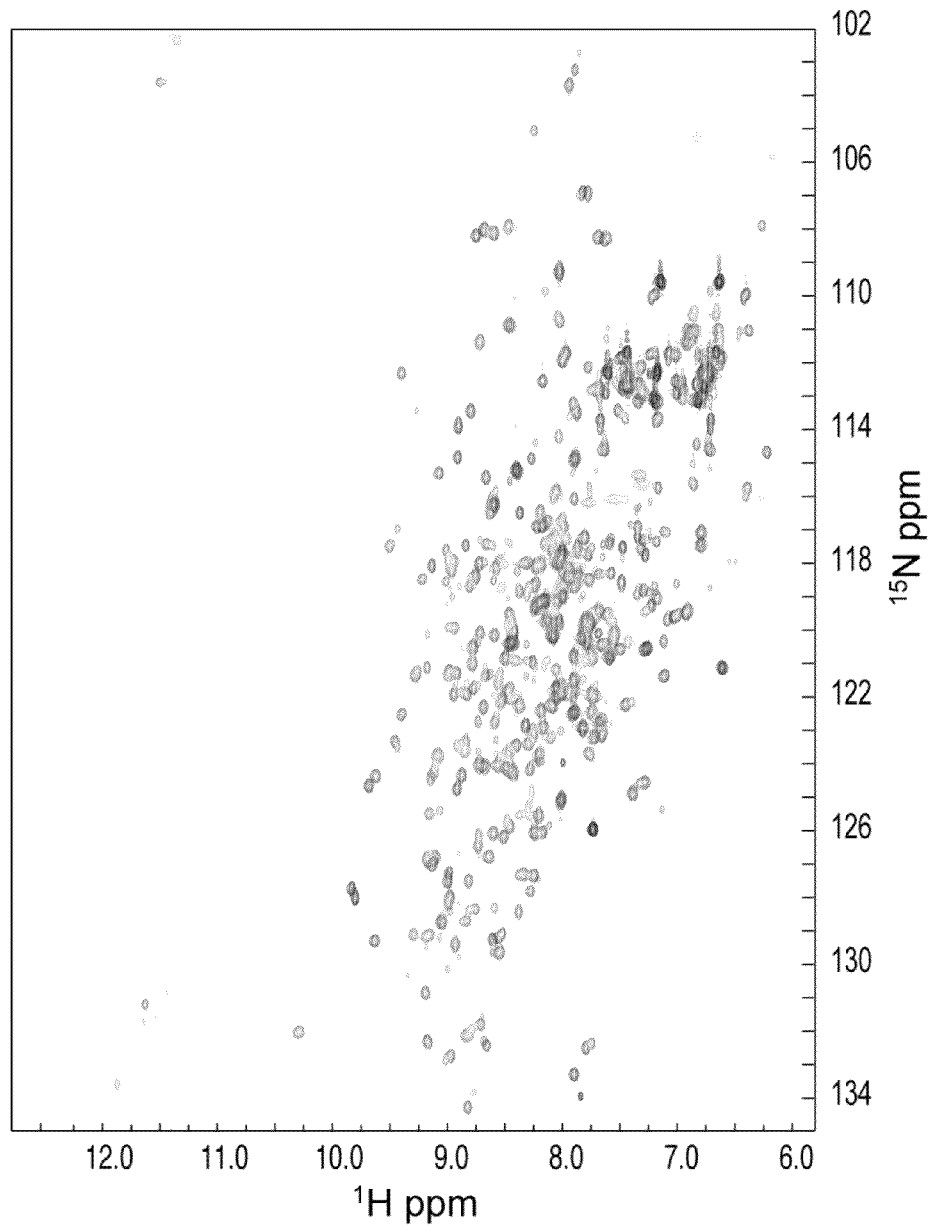
FIG. 5 is a graph of NMR data showing that TePixJ GAF (C555A) is a stable monomer.

FIG. 5 shows that TePixJ GAF (C555A) is a stable monomer. NMR HSQC (H—$^{15}$N correlation) of TePixJ GAF domain with C555A mutation in the blue-absorbing ground state (Pb) and green-absorbing excited state (Pg). ppm=parts per million. Peak intensity indicates the sample is a monomer at concentrations greater than 1 mM.

Two-dimensional HSQC $^1$H—$^{15}$N correlation spectra of the [$^{15}$N]-PCB TePixJ-GAF sample in the dark-adapted (Pb) state revealed four distinct N—H crosspeaks, with $^{15}$N chemical shifts of 127.5, 131.25, 132.25, and 135.25 ppm representative of all four PCB pyrrole amides. These data were in contrast to the [$^{15}$N]-PCB SyB-Cph1 sample where only one amide group was observed, most likely due to solvent exchange. The data showed unambiguously that all four nitrogens are protonated in the Pb dark-adapted state. The most down-field crosspeak at approximately 10.25 ppm in the $^1$H dimension is most certainly hydrogen bonding or forming a salt bridge interaction given its unusually high chemical shift. Upon irradiation with blue light all four N—H peaks were again evident, demonstrating unambiguous protonation in the Pg excited state. Aside from a doubling of the 132.25 ppm peak suggesting a minor conformational exchange between two stable states, only the 135.25 peak experienced a significant change in its chemical environment. This peak showed a marked increase in shielding by reappearing up-field at 9 ppm in the Pg HSQC spectrum CH coordinate), suggesting one or more chemical bonds breaking during Pb to Pg photoconversion (e.g. hydrogen bond). Taken together, the protonated pyrrole nitrogens in both Pb and Pg states demonstrate that the TePixJ GAF domain alone is fully protected from the solvent in both ground and excited conformers, and that only one of the N—H moieties experiences a significant change in its chemical environment during photoconversion.

Previously, several models have been proposed regarding the precise Cys-494 attachment site to the cyanochrome PCB bilin, the favored model proposing a reversible thioether linkage at the PCB B-C methine bridge (C10). An alternative hypothesis points to a C10 Cys breakage with blue light exposure and a reestablishment of the linkage at the A-B methine bridge (C4) in Pg. To gain additional insight as to where the TePixJ Cys-494 might be attaching to the bilin, a [$^{13}$C]-PCB labeling scheme similar to van Thor et al., 2006, *Biophys. J.* 91: 1811-1822, was used, whereby all methine bridge carbons could be monitored during photoconversion. To incorporate $^{13}$C into PCB methine carbons (and others), 5-[$^{13}$C]-ALA was added to the TePixJ-GAF expression strain media during growth and the resultant 5-C$^3$C]-PCB TePixJ GAF protein harvested and purified. Changes in PCB $^{13}$C were monitored using NMR in one-dimension (by $^{13}$C direct detection) and two dimensions (by $^1$H—$^{13}$C HSQC) in both Pb and Pg states. Combined one-dimensional and two-dimensional Pb spectra showed four distinct $^{13}$C peaks at 108.25 ppm, 108.75 ppm, and two at 110 ppm ($^{13}$C dimension) within the methine region. When irradiated with blue light all these peaks disappear to reemerge as an intense singlet at 102.5 ppm ($^{13}$C dimension). These results point to significant chemical changes occurring within the methine bridges of TePixJ chromophore during Pb to Pg photoconversion.

Potential for Use of the Generated Mutants with Fluorescence Resonance Energy Transfer (FRET) Applications.

Figure 6:
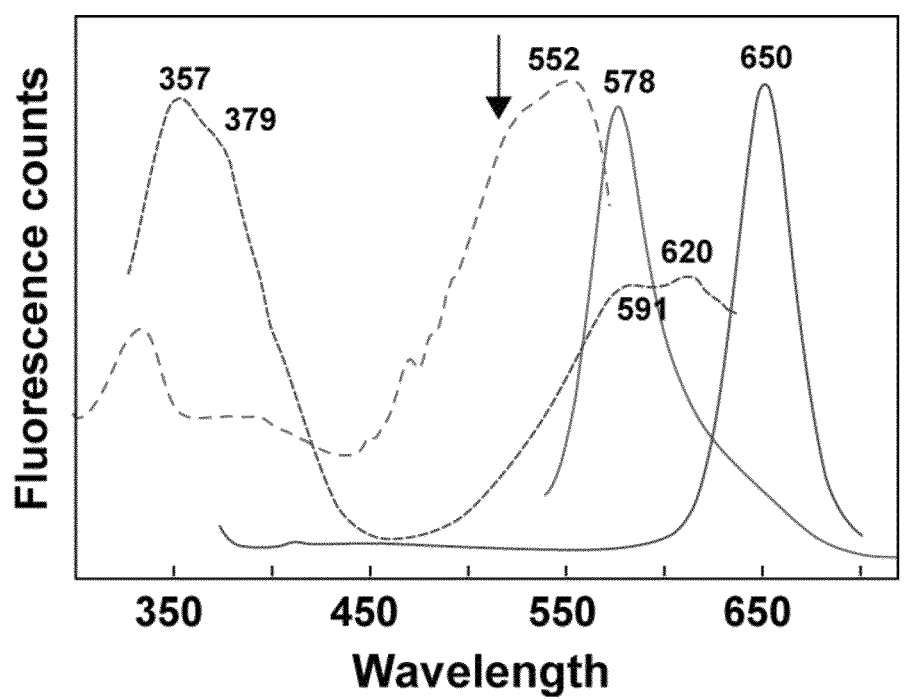
FIG. 6 is a graph illustrating how TePixJ (D492H) and SyB-Cph1 (D86H) have potential for use with Fluorescence Resonance Energy Transfer (FRET) technology.

FIG. 6 illustrates how TePixJ (D492H) and SyB-Cph1 (D86H) have potential for use with Fluorescence Resonance Energy Transfer (FRET) technology. Depicted in FIG. 6 is superimposition of scanning fluorescence excitation and emission spectra from TePixJ GAF (D492H) and SyB-Cph1 GAF-PHY (D86H). Excitation of TePixJ (D492H) at approximately 500 nm (indicated by the arrow) will produce an emission of approximately 578 nm (broad dotted line) that should, in turn, excite SyB-Cph1 at approximately 591 nm (short dotted line) giving a measurable emission peak of approximately 650 nm in the red part of the light spectrum: Excitation spectra are given as dotted lines and emission spectra as solid lines. Other mutants generated in accord with this invention could be used for FRET applications as well.

The TePixJ GAF Cys-494 Thioether Linkage Remains after Blue Light Irradiation.

FIG. 7 illustrates how the TePixJ GAF Cys-494 thioether linkage remains after blue light irradiation. A TePixJ C552A mutation was constructed to eliminate the canonical cysteine thioether linkage to the 3$^1$ carbon of the PCB chromophore. FIG. 7A: Purified protein was then either irradiated with intense blue light (430 nm) for 15 minutes to convert it to Pg, or left in the dark (remained in Pb). The sample was then boiled in SDS-PAGE gel loading buffer containing 2mercaptoethanol and subjected to denaturing electrophoresis. The resultant gel was then incubated with zinc acetate and PCB incorporation was assayed for by exposure to UV light (labeled Zinc). The gel was then Coomassie stained for assessment of protein content and purity (labeled Protein). FIG. 7B 50 µl samples of either purified wild-type or C522A TePixJ GAF chromoprotein were aliquoted into PCR strip tubes in the dark (Pb state) and immediately photographed under white light. After 15 minutes of white light exposure the samples were again photographed (Pg state). Notice the deep red color associated with the wild-type TePixJ photoconversion to Pg not present in the C522A mutant. FIG. 7C: UV-vis absorbance spectra of the TePixJ GAF C522A variant after purification in the dark (Pb state, solid line) and post blue light irradiation (dotted line). Instead of a Pg-like absorbance profile, peaks at 385 and 609 nm were observed. FIG. 7D: Diagram of the probably chemical structure of the C552A chromophore post ligation to the apoprotein. Note that the double bond at the 3$^1$ carbon where Cys-522 would normally attach to the bilin though a thioether linkage. Under this scenario, the only covalent linkage to the protein would be through Cys-494.

NMR Analysis of $^{15}$N-Labeled TePixJ GAF in Po and Pb States.

In previous work the inventors demonstrated that an isolated GAF domain chromopeptide could be successfully isotopically labeled for NMR analyses of global movements in protein structure during photoconversion (Ulijasz et a/., 2008). In this study a similar strategy was used with the TePixJ GAF chromopeptide. Recombinant protein was expressed in minimal media containing $^{15}$NH$_4$Cl as the sole nitrogen source and purified using a combination of Nickel-affinity chelate chromatography and FPLC separation steps. The final product was concentrated and NMR $^1$H—$^{15}$N two-dimensional correlations were acquired in both Pb and Pb states.

Figure 8:
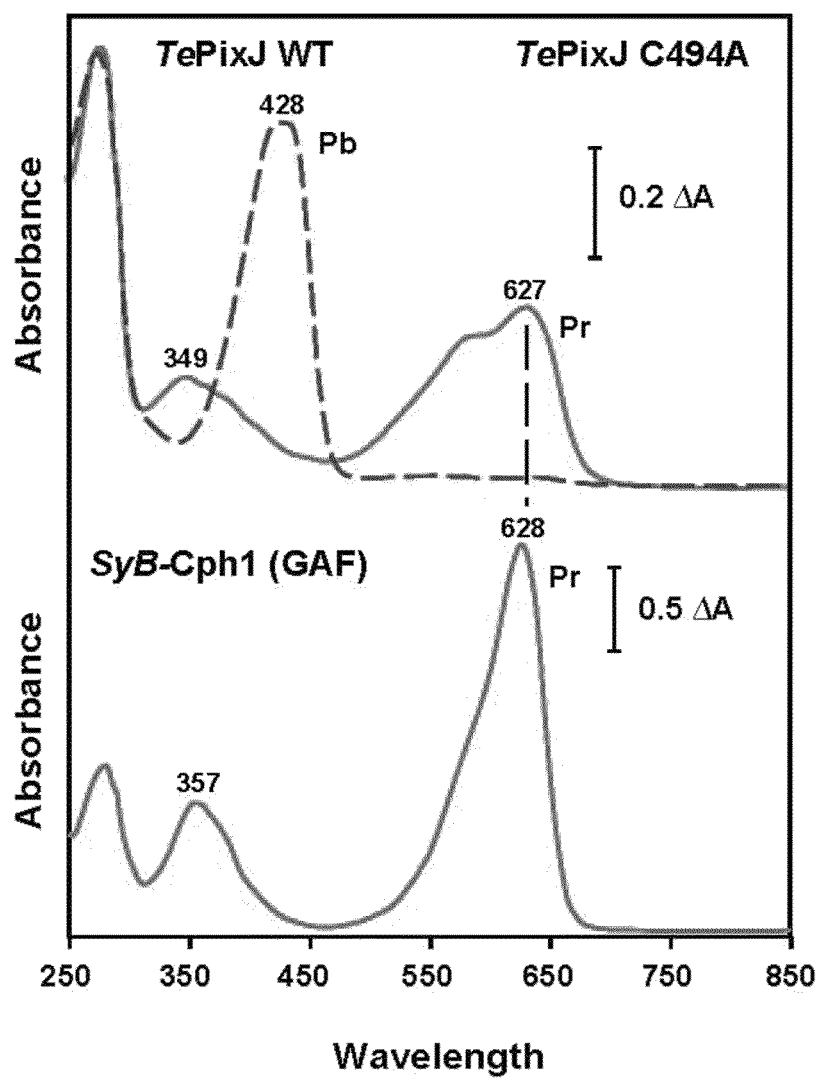
FIG. 8 is a graph depicting how the TePixJ GAF mutant C522A. spectra resembles that of SyB-Cph1.

FIG. 8 illustrates how the TePixJ GAF mutant C522A spectra resembles that of SyB-Cph1. The UV-vis spectra profile of wild-type TePixJ GAF in the dark adapted state (Pb) is represented by the blue dotted line (peak chromoprotein absorbance 430 nm), the C522A mutant by the solid line above (top), and SyB-Cph1 GAF (wild-type) by the solid line below (bottom). Note the almost identical chromoprotein peak absorbance of TePixJ GAF C522A and SyBCph1 GAF wild-type (627/628 nm), suggesting similar chromophore conformations and protein-chromophore contacts.

FIG. 8 depicts an overlay plot of TePixJ GAF Pb and Pg $^1H$—$^{15}N$ HSQC spectra with a C555A substitution. This variant was used because although wild-type spectra indicated a monomeric form, these samples consistently observed moderate peak broadening indicative of multiple states (data not shown). Since Cys-555 was predicted to be solvent exposed, this effect might be due to due to transient disulfide bond formation or loss of the chromophore in solution. Conversely, the C555A variant enabled cleaner spectra with little peak broadening and a short data acquisition time, indicating TePixJ GAF (C555A) remains a monomer in two more distinct conformers (FIG. 8). Moreover, as suggested by a lack of an absorbance spectra isosbestic point (FIG. 3), the Pb and Pg HSQCs revealed two nonoverlapping structural entities (FIG. 8) that were reversible upon green light irradiation (data not shown). Over 50% of the predicted 163 amino acids within the TePixJ GAF (C555A) sequence showed an appreciable chemical shift, with several peaks becoming completely isolated from their Pb counterparts (FIG. 8). Some smaller secondary peaks were also observed which could indicate a minor subspecies, or multiple stable conformations of several amide groups. An additional $^1H$—$^{15}N$ HSQC taken five days after photoconversion revealed no evidence of dark reversion (data not shown). Taken together, these data demonstrate that an entirely new TePixJ protein structure is obtained after photoconversion to Pb, and that both Pb and Pg structures may now be solved by collection of three-dimensional data from a uniformly labeled $^{15}N$—$^{13}C$ sample.

Prophetic Example 1

Reconstitution of Modified TePixJ in *C. elegans* Cells

Transformation of the nematode *Caenorhabditis elegans* with a vector containing TePixJ with a D492A or C494H substitution under the control of the promoter of the *C. elegans* mec-7 gene will result in the production of fluorescent cells. Live animals are mounted on agar pads with 10 mM $NaN_3$ as an anesthetic and examined using either a Zeiss universal or axiophot microscope with a long-pass or bandpass emission filter.

Cells expressing the modified TePixJ proteins may be conveniently separated using a fluorescence-activated cell sorter.

Prophetic Example 2

Use of TePixJ to Monitor Protein Trafficking

TePixJ with a D492A or C494H substitution is fused to the pleckstrin homology (PH) domain of human AKT1. The PH domain to binds to phosphatidylinositol-3,4,5-trisphosphate formed at the plasma membrane after growth factor stimulation. Serum-starved HEK293 cells expressing the TePixJ-PH$^{AKT1}$ fusion show fluorescence diffusely distributed in the cytosol. The signal is expected to translocate to the plasma membrane within 10 min after insulin stimulation, illustrating that TePixJ can image the trafficking of fusion proteins.

Prophetic Example 3

Expression of Modified TePixJ in Mice

Adenoviruses that express modified TePixJ having a C494H or C494A substitution are created by first constructing a transcription unit comprising the coding sequence for the modified TePixJ and the poliovirus internal ribosome entry sequence IRES by assembly PCR. The transcription unit is cloned into pENTR1a (Invitrogen), and transferred into pAd-CMV-DEST (Invitrogen) using Gateway recombinase (Invitrogen). Viruses are produced in HEK293 cells by transfection, undergo one round of amplification, before being purified by anion exchange chromatography.

Albino C57BL/6 mice (Jackson Labs) are injected with $2 \times 10^9$ infectious units of adenovirus via tail vein. After 5 days, the belly fur is removed using a depilatory cream. Mice are imaged on a spectral imager (e.g. Maestro, Cambridge Research Instruments). The IFP channel is excited with a 590-600 nm (center wavelength/full width at half maximum) bandpass filter with the imager's tunable emission filter at 650 nm.

Expression of the modified TePixJ in intact mice via adenovirus is expected to produce red to near infrared fluorescence.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art of genetics, molecular biology, and biochemistry, are within the scope of this invention. All publications, patents; and patent applications cited herein are incorporated by reference in their entirety for all purposes.

SUMMARY OF SEQUENCE LISTINGS

SEQ ID NO: 1 is the amino acid sequence of the GAF domain of the *Thermosynechococcus elongatus* cyanobacteriochrome with the C-terminal "SLHHHHHH" (SEQ ID NO: 3) sequence provided by the pBAD protein expression vector. SEQ ID NO: 1 is GenBank locus number tll0569, residues 430591.

SEQ ID NO: 2 is the full-length amino acid sequence of the chromophore-binding domain of cyanobacteriochrome isolated from *Thermosynechococcus elongatus*. SEQ ID NO: 2 is GenBank locus number tl10569, residues 1-940.

SEQ ID NO: 3 is the C-terminal sequence SLHHHHHH provided by the pBAD protein expression vector.

SEQ ID NO: 4 is a sequence of a TePixJ GAF F1 primer.
SEQ ID NO: 5 is a sequence of a TePixJ GAF F2 primer.
SEQ ID NO: 6 is a sequence of a TePixJ GAF R1 primer.
SEQ ID NO: 7 is a sequence of a TePixJ GAF R2 primer.
SEQ ID NO: 8 is a sequence of a C522A-F primer.
SEQ ID NO: 9 is a sequence of a C522A-R primer.
SEQ ID NO: 10 is a sequence of a C555A-F primer.
SEQ ID NO: 11 is a sequence of a C555A-R primer.
SEQ ID NO: 12 is a sequence of a R459A-F primer.
SEQ ID NO: 13 is a sequence of a R459A-R primer.
SEQ ID NO: 14 is a sequence of a D494N-F primer.
SEQ ID NO: 15 is a sequence of a D492N-R primer.
SEQ ID NO: 16 is a sequence of a D494A-F primer.
SEQ ID NO: 17 is a sequence of a D492A-R primer.
SEQ ID NO: 18 is a sequence of a D494H-F primer.
SEQ ID NO: 19 is a sequence of a D492H-R primer.
SEQ ID NO: 20 is a sequence of a Q509A-F primer.
SEQ ID NO: 21 is a sequence of a Q509A-R primer.
SEQ ID NO: 22 is a sequence of a R507A-F primer.
SEQ ID NO: 23 is a sequence of a R507A-R primer.
SEQ ID NO: 24 is a sequence of a Y463H-F primer.

SEQ ID NO: 25 is a sequence of a Y463H-R primer.
SEQ ID NO: 26 is a sequence of a D492H-F primer.
SEQ ID NO: 27 is a sequence of a D492H-R primer.
SEQ ID NO: 28 is a sequence of a C494H-F primer.
SEQ ID NO: 29 is a sequence of a C494H-R primer.
SEQ ID NO: 30 is a sequence of a C494A-F primer.
SEQ ID NO: 31 is a sequence of a C494A-R primer.
SEQ ID NO: 32 is the amino acid sequence of a GAF domain containing fragment of TePixJ from *Thermosynechococcus elongates*.
SEQ ID NO: 33 is the amino acid sequence of a GAF domain containing fragment of Syn-TaxD1 from *Synechocystis* sp.
SEQ ID NO: 34 is the amino acid sequence of a GAF domain containing fragment from *Cyanothece* sp.
SEQ ID NO: 35 is the amino acid sequence of a GAF domain containing fragment from *Acaryochloris marina*.
SEQ ID NO: 36 is the amino acid sequence of a GAF domain containing fragment from *Gloeobacter violaceus*.
SEQ ID NO: 37 is the amino acid sequence of a GAF domain containing fragment of Syn-ETR from *Synechocystis* sp.
SEQ ID NO: 38 is the amino acid sequence of a GAF domain containing fragment of TeClkA from *Thermosynechococcus elongates*.
SEQ ID NO: 39 is the amino acid sequence of a GAF domain containing fragment of Syn-CikA from *Synechocystis* sp.
SEQ ID NO: 40 is the amino acid sequence of a GAF domain containing fragment of Ana-CikA from *Anabaena variabilis*.
SEQ ID NO: 41 is the amino acid sequence of a GAF domain containing fragment of RcaE from *Fremyella diplosiphon*.
SEQ ID NO: 42 is the amino acid sequence of a GAF domain containing fragment of SyB-Cph1 from *Synechococcus* sp.
SEQ ID NO: 43 is the amino acid sequence of a GAF domain containing fragment of DrBphP from *Deinococcus radiodurans*.
SEQ ID NO: 44 is the amino acid sequence of a GAF domain containing fragment of Syn-Cph1 from *Synechocystis* sp.
SEQ ID NO: 45 is the amino acid sequence of a GAF domain containing fragment of AtPhyA from *Arabidopsis thaliana*.

---

What is claimed is:

1. A recombinant polynucleotide comprising a nucleotide sequence that encodes a modified blue/green light absorbing *Thermosynechococcus elongatus* phytochrome domain, wherein the modified phytochrome domain comprises an amino acid sequence that has at least 85% amino acid sequence identity to the amino acid sequence of amino acids 1 to 162 of SEQ ID NO: 1, wherein the modified phytochrome domain has (a) an amino acid other than Asp at the residue corresponding to position 63 of SEQ ID NO: 1 or (b) an amino acid other than Asp at the residue corresponding to position 63 of SEQ ID NO: 1 and an amino acid other than Cys at the residue corresponding to position 65 of SEQ ID NO: 1, and wherein the modified phytochrome domain has increased fluorescent activity compared with the fluorescent activity of a phytochrome domain comprising the amino acid sequence of amino acids 1 to 162 of SEQ ID NO: 1.

2. The recombinant polynucleotide of claim 1, wherein the modified phytochrome domain comprises an amino acid sequence that has at least 95% amino acid sequence identity to the amino acid sequence of amino acids 1 to 162 of SEQ ID NO: 1.

3. The recombinant polynucleotide of claim 1, wherein the modified phytochrome domain further has an amino acid other than Cys at the residue corresponding to position 126 of SEQ ID NO: 1.

4. An expression vector comprising the recombinant polynucleotide of claim 1 and a regulatory sequence operably linked to the polynucleotide.

5. An isolated cell comprising a DNA molecule, wherein the DNA molecule comprises the recombinant polynucleotide of claim 1 and a regulatory sequence from a gene other than a gene encoding a bacterial phytochrome, wherein the regulatory sequence is operably linked to the recombinant polynucleotide, wherein (i) the cell is selected from the group consisting of a bacterial cell, a yeast cell, a fungal cell, a plant cell, an insect cell, a nematode cell, an animal cell, and a human cell and (ii) the cell expresses the recombinant polynucleotide.

6. A method for detecting expression of a regulatory sequence in a cell, the method comprising:

a) providing an isolated cell comprising a DNA molecule, wherein the DNA molecule comprises the recombinant polynucleotide of claim 1 and the regulatory sequence, wherein the regulatory sequence is operably linked to the recombinant polynucleotide,
b) culturing the cell under conditions such that the regulatory sequence directs expression of the modified phytochrome domain; and
c) detecting the modified phytochrome domain in the cell, thereby detecting expression of the regulatory sequence in the cell.

7. The method of claim 6, wherein the modified phytochrome domain comprises an amino acid sequence that has at least 95% amino acid sequence identity to the amino acid sequence of amino acids to 162 of SEQ ID NO: 1.

8. The method of claim 6, further comprising adding a fluorescent adduct to the cell.

9. A method for producing a fluorescent molecular weight protein marker, the method comprising:
a) providing an isolated cell comprising a DNA molecule encoding a fusion protein with known molecular weight, wherein the DNA molecule comprises the recombinant polynucleotide of claim 1 and a nucleic acid encoding a known amino acid sequence in the same reading frame,
b) culturing the cell under conditions suitable for expressing the DNA molecule, thereby expressing the fusion protein, and
c) recovering the fusion protein expressed in step b), thereby producing a fluorescent molecular weight protein marker.

10. The method of claim 9, wherein step b) is performed in the presence of a fluorescent molecule capable of forming a fluorescence adduct with the fusion protein.

11. The method of claim 9, wherein the fusion protein is expressed in *Escherichia coli*.

12. The method of claim 9, further comprising purifying the fusion protein.

13. The recombinant polynucleotide of claim 1, wherein the modified phytochrome domain has an amino acid other than Asp at the residue corresponding to position 63 of SEQ ID NO: 1 and wherein the amino acid other than Asp is selected from the group consisting of His, Asn, and Ala.

14. The recombinant polynucleotide of claim 1, wherein the modified phytochrome domain has an amino acid other than Asp at the residue corresponding to position 63 of SEQ ID NO: 1 and an amino acid other than Cys at the residue corresponding to position 65 of SEQ ID NO: 1.

15. The recombinant polynucleotide of claim 14, wherein the amino acid other than Asp at the residue corresponding to position 63 of SEQ ID NO: 1 is selected from the group consisting of His, Asn, and Ala, and the amino acid other than Cys at the residue corresponding to position 65 of SEQ ID NO: 1 is His or Ala.

16. The recombinant polynucleotide of claim 3, wherein the amino acid other than Cys at the residue corresponding to position 126 of SEQ ID NO: 1 is Ala.

* * * * *